(12) United States Patent
Parrini et al.

(10) Patent No.: US 12,207,976 B2
(45) Date of Patent: Jan. 28, 2025

(54) SYSTEM FOR PERFORMING ROBOT-ASSISTED SURGERY

(71) Applicant: Epica International, Inc., San Clemente, CA (US)

(72) Inventors: Gianluca Parrini, Cascina (IT); Luca Ferretti, Pisa (IT); Luca Bosio, Pisa (IT)

(73) Assignee: EPICA INTERNATIONAL, INC., San Clemente, CA (US)

( * ) Notice: Subject to any disclaimer, the term of this patent is extended or adjusted under 35 U.S.C. 154(b) by 810 days.

(21) Appl. No.: 17/331,457

(22) Filed: May 26, 2021

(65) Prior Publication Data
US 2021/0369389 A1    Dec. 2, 2021

Related U.S. Application Data

(60) Provisional application No. 63/030,299, filed on May 26, 2020.

(51) Int. Cl.
*A61B 90/11* (2016.01)
*A61B 34/30* (2016.01)
*A61B 90/00* (2016.01)
*A61B 90/50* (2016.01)

(52) U.S. Cl.
CPC ............. *A61B 90/11* (2016.02); *A61B 34/30* (2016.02); *A61B 90/37* (2016.02); *A61B 90/50* (2016.02); *A61B 2090/3762* (2016.02)

(58) Field of Classification Search
CPC ......... A61B 90/11; A61B 90/37; A61B 90/50; A61B 2090/3762; A61B 34/30
See application file for complete search history.

(56) References Cited

U.S. PATENT DOCUMENTS

| 4,608,977 A | * | 9/1986 | Brown | A61B 90/11 378/162 |
| 5,201,742 A | * | 4/1993 | Hasson | A61B 90/11 606/1 |
| 5,752,962 A | * | 5/1998 | D'Urso | A61B 90/11 128/857 |
| 5,891,157 A | | 4/1999 | Day et al. | |
| 2009/0234369 A1 | * | 9/2009 | Bax | A61B 34/30 606/130 |

(Continued)

FOREIGN PATENT DOCUMENTS

WO    2017/134546 A2    8/2017

OTHER PUBLICATIONS

Brown, "The Mathematics of the N-Localizer for Stereotactic Neurosurgery." Cureus 5(10): e142, Oct. 25, 2013, pp. 1-17.

(Continued)

*Primary Examiner* — Chao Sheng
(74) *Attorney, Agent, or Firm* — STEPTOE LLP; Carl B. Wischhusen

(57) ABSTRACT

An apparatus for performing surgery includes a first link that includes a first end and a second end, a second link that includes a first end and a second end, and an end effector positioned at the first end of the first link. The first end of the second link is coupled to the first link by a hinge. The end effector traces along a surface, which may be spherical or hemispherical. A system that includes the apparatus and an imaging device, such as a CT scanner, is also described.

26 Claims, 37 Drawing Sheets

(56) References Cited

U.S. PATENT DOCUMENTS

| | | | |
|---|---|---|---|
| 2011/0237881 A1* | 9/2011 | Kunz | A61B 1/3132 |
| | | | 600/106 |
| 2013/0282022 A1* | 10/2013 | Yousef | A61B 90/11 |
| | | | 606/130 |
| 2017/0000497 A1 | 1/2017 | Wolfe et al. | |
| 2017/0014200 A1* | 1/2017 | Onuma | A61B 17/3403 |

OTHER PUBLICATIONS

Brown, "The Mathematics of Three N-Localizers Used Together for Stereotactic Neurosurgery." Cureus 7(10): e341, Oct. 2, 2015, pp. 1-21.

Elekta, "Leksell Stereotactic System® Overview." 22 pages, retrieved on Apr. 21, 2020 from https://www.elekta.com.

Inomed, "RM stereotactic system." 2 pages, retrieved on Apr. 21, 2020 from https://www.en.inomed.com/products/functional neuro-surgery/stereotactic-systems/rm-stereotactic-system/.

International Search Report and Written Opinion from International Patent Application No. PCT/US2021/034357, mailed Oct. 4, 2021, 11 pages.

* cited by examiner

SYSTEM FOR PERFORMING ROBOT-ASSISTED SURGERY

CLAIM OF PRIORITY

This application claims priority from U.S. Provisional Application No. 63/030,299, filed on May 26, 2020, which is incorporated by reference in its entirety.

BACKGROUND

Various functional neurosurgery operations or procedures involve implantation of electrodes or other components. These operations, including deep brain stimulation, stereoelectroencephalography, and hemorrhagic stroke treatment, require a high degree of accuracy in locating the target of a stimulating device as well as its trajectory. Such neurosurgical procedures often involve intra-operative imaging, so it is important to avoid artifacts during the image acquisition caused by surgical instruments and mechanical components.

Figure 1:
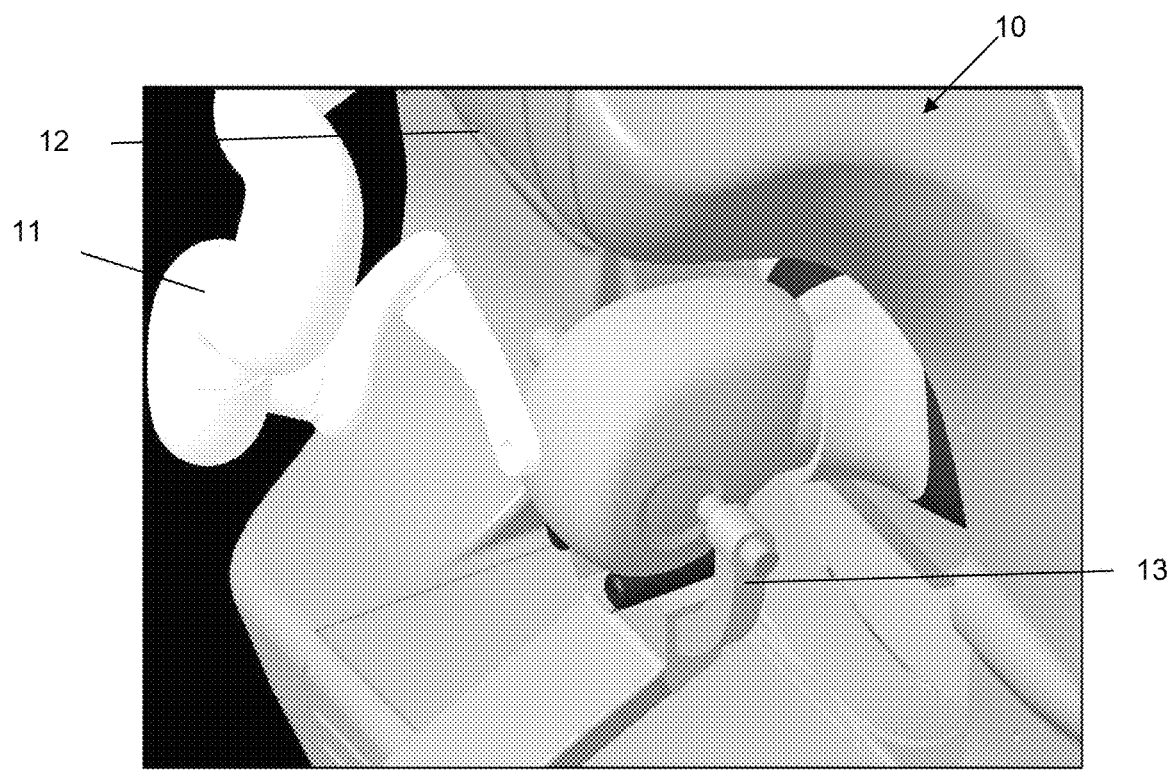
FIG. 1 shows a system including an articulated arm attached to the top of a CT scanner.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

For example, various functional neurosurgery operations or procedures involve implantation of electrodes or other components. These operations, deep brain stimulation, stereoelectroencephalography, and hemorrhagic stroke treatment, are described here for reference. Deep brain stimulation (DBS) is a neurosurgical procedure in which an electrode (neurostimulator) is implanted in the brain to supply electrical impulses to a specific target area. DBS may be used to treat Parkinson's disease and other medical conditions involving tremors. Placement of neurostimulators requires a high degree of accuracy. The electrodes may be placed deep inside the patient's brain. The trajectory of the insertion needle must be very accurate in order to avoid damage to other parts of the brain structure, otherwise severe medical complications may result. DBS is performed using intra-operative imaging, such as magnetic resonance imaging (MRI). Pre-operative imaging of patient is usually performed before the operation. The software used in the surgery can perform fusion between the pre-operative imaging and the intra-operative imaging. A non-limiting example of such fusion can be between an MRI scan and a computed tomography (CT) scan. Implantation can be performed under local anesthesia or under general anesthesia (depending on the medical condition of the patient). The patient's head is fixed on a patient bed using a frame-based or frameless headset, and the probe electrode is inserted using a stereotactic assembly. The patient lays on the bed in a supine position. A hole (about 14 mm in diameter) is drilled into the patient's skull using a cranial drill. The drilling position in the skin and skull can be marked with a surgical pen/pencil using a stereotactic headframe.

Stereoelectroencephalography (SEEG) is a surgical procedure involving the placement of electrodes in a targeted area of the brain. SEEG can reach areas deep in the brain. This procedure is commonly used and is a minimally invasive approach to identify the origin of epileptic seizures. SEEG can be considered an evolution of conventional electroencephalography (EEG). To implant the electrodes, the surgeon makes ten to twenty (depending on the patient) small incisions in the scalp and skull, with minimal blood loss. SEEG surgery lasts about four hours and requires general anesthesia, but removal of the electrodes is a simple procedure that takes only ten to fifteen minutes under local anesthesia.

A hemorrhagic stroke is bleeding (hemorrhage) that suddenly occurs and interferes with the brain's function. The hemorrhage could be located in different sites in the brain. This condition can be treated with stereotactic aspiration assisted by intra-operative computed tomography (CT), which helps locate the hemorrhage site, and a specially developed suction tool to drain it. The patient is immobilized in a stereotactic head frame that allows a greater degree of precision and accuracy than otherwise possible. Since hemorrhagic stroke is considered a medical emergency (high fatality rate and immediate treatment required), it is usually treated in the Intensive Care Unit (ICU).

These neurosurgery procedures require a high degree of accuracy in both locating the target of the procedure, e.g., an electrode or a stroke site, and guiding an instrument's trajectory to place the electrode or drain the site. These procedures often involve intra-operative imaging, such as, but not limited to CT, digital radiography, fluoroscopy, or MRI. They are also often performed with the assistance of a robot. For example, while treating hemorrhagic stroke, it may be useful to have a CT-mounted robot performing a fast detection of the site of the hemorrhage, to allow for quick and precise positioning and draining.

These neurosurgery procedures use stereotactic devices to assist in the surgery. Four different kinds of stereotactic devices are described below: (1) an orthogonal system; (2) a burr-hole mounted system; (3) an arc-quadrant system; and (4) an arc-phantom system.

In a simple orthogonal system, a probe is directed perpendicular to a square base unit fixed to the skull. This provides three degrees of freedom by means of a carriage that moves orthogonally along the base plate or along a bar attached parallel to the base plate of the instrument. Attached to the carriage is a second track that extends perpendicularly across a head frame.

A burr-hole mounted system provides a limited range of possible intracranial target points with a fixed entry point. It provides two angular degrees of freedom and a depth adjustment. A surgeon can place the burr hole over non-essential brain tissue and can use an instrument to direct a probe to the target point from the fixed entry point at the burr hole.

In an arc-quadrant system, a probe is directed perpendicular to the tangent of an arc (which rotates about the vertical axis) and a quadrant (which rotates about the horizontal axis). The probe, directed to a depth equal to the radius of the sphere defined by the arc-quadrant, always arrives at the center or a focal point of that sphere.

In an arc-phantom system, an aiming bow attached to a head ring and fixed to a patient's skull can be transferred to a similar ring that contains a simulated target. In this system, a phantom target is moved on the simulator to 3D coordinates. After adjusting a probe holder on the aiming bow so that the probe touches the desired target on the phantom, the transferable aiming bow is moved from the phantom base ring to the base ring on the patient. The probe is then lowered to the determined depth in order to reach the target point deep in the patient's brain.

Examples of stereotactic devices are the Leksell® head frame, inomed RM stereotactic system, and the N-localizer.

The Leksell® head frame (manufactured by Elekta AB) is a device that can be used to perform a DBS procedure. (Other similar devices may also be used for this type of procedure.) The Leksell Stereotactic System includes the Leksell® coordinate frame and the Leksell® multipurpose stereotactic arc. The Leksell® head frame includes a support that holds an end effector (e.g., a needle). The support slides along the multipurpose stereotactic arc, which is pivotally coupled to revolute joints disposed coaxially to allow the arc to rotate around the R axis. The Leksell Stereotactic System provides globally five degrees of freedom. The system may include an optional Elekta MicroDrive™ that includes a passive slider, manually actuated by a leadscrew, which can be mounted on the support to provide a sixth degree of freedom allowing radial motion of the end effector. This permits a fine adjustment of the insertion depth.

The inomed RM stereotactic system is a high-precision system with a high level of stability and precision. It includes three fixation points. This system can be used for DBS, pallidotomy, thalamotomy, brachytherapy, stereotactic biopsy, and SEEG depth electrodes.

The N-localizer (also called "N-bar") is a device that enables guidance of a stereotactic surgery or radiosurgery based on imaging. The N-localizer includes a diagonal rod that allows calculating the point where a tomographic image plane intersects the diagonal rod. This system is disclosed in U.S. Pat. No. 4,608,977; Russell Brown, "The Mathematics of the N-Localizer for Stereotactic Neurosurgery," Cureus vol. 5, no. 10 (2013); and Russell Brown, "The Mathematics of Three N-Localizers Used Together for Stereotactic Neurosurgery," Cureus vol. 7, no. 10 (2015).

Besides needing to accurately locate the target and the trajectory for accessing the target, there are other issues to consider when using robot-assisted neurosurgery to perform functional neurosurgery procedures in conjunction with an imaging system. These issues include the hindrance of the imaging system, the patient's body, the patient's bed, the presence of surgical instruments (e.g., depressors, needle guides, draining surgical instruments, etc.) that are manually operated by a surgeon or inserted into a patient's tissues during the operation, and that the workspace for the robot should keep enough free space around a patient's head. Furthermore, a surgeon performing a manual operation during such a procedure should be able to freely access the upper part of a patient's skull. To do so, a removable section or a "parking position" may be provided on the robot. Moreover, the system should be quickly movable and easily repositionable to reduce procedure time, minimize the risk of medical complications, and reduce a surgeon's stress. In addition, an automated system could considerably reduce the effort expended by the medical staff. Easy sterilization and cleaning of the system play an important role to prevent medical complication caused by infection and to reduce set-up time. Further, a surgeon needs enough degrees of freedom to carry out a surgical operation to locate a surgical instrument at a given position and orientation and to adjust an insertion depth. At the same time, the spanning area should be wide enough to perform the surgical operation (also considering patients' anatomical differences). Also, a dynamic control issue (i.e., a singularity) can occur due to the kinematic design. Such issues are addressed by the present invention.

During the operation, the surgeon can have a free access to a patient's head. A rest area for the device can be provided in order to reduce the encumbrance. Furthermore, the system can be removed from the area of interest to avoid artifact in the imaging acquisition. In order to obtain high degree of precision, a surgical robot can be mechanically linked to an imaging device. In certain embodiments, the imaging device may be a CT scanner, and the surgical robot may be mechanically linked to a CT gantry, in accordance with PCT Pub. No. WO 2017/134546 and U.S. Pat. No. 10,772,577, each of which is incorporated by reference in its entirety. The number of degrees of freedom suitable for the surgical operation can also be considered. High precision and repeatability are important. A headset should be normally connected (not rigidly) on the bed, connectible in a rigid way to the CT scanner. For safety during the surgical operation, the patient's bed should be able to be quickly moved away from the CT scanner.

Figure 2:
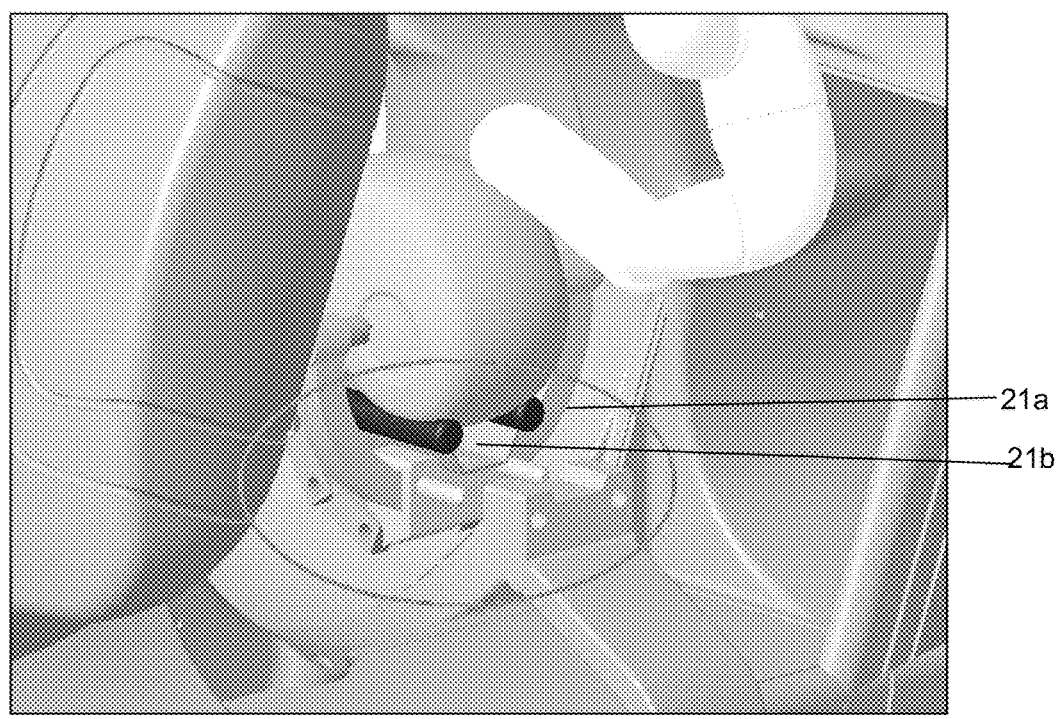
FIG. 2 shows a model of a frameless headset having a pair of pins for coupling a patient bed to the CT scanner.
Figure 3:
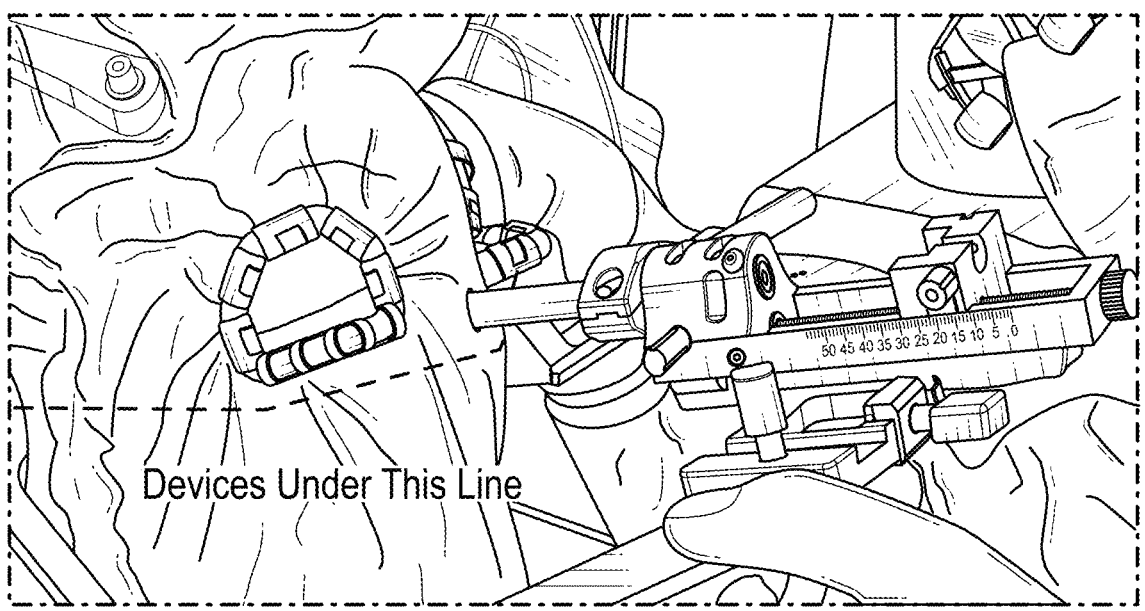
FIG. 3 shows a deep brain stimulation (DBS) procedure.

Reference is now made to FIG. 1, which shows robot-assisted surgery system 10. System 10 includes articulated arm 11 attached to the top of CT scanner 12. A patient's head is fixed on frameless headset 13, which is rigidly connected to the patient bed. A robot can be mounted on the top of the gantry (in accordance with, e.g., U.S. application Ser. No. 16/402,002 (U.S. Pat. Pub. No. 2019/0336093), which is incorporated by reference in its entirety). The headset is connected (not rigidly) to the patient bed. The headset may be connected to the CT gantry using two pins 21a, 21b as shown in FIG. 2, allowing a fast disconnection in case of emergency. This configuration is not suitable for the DBS procedure because all the instruments must be located toward the lower part of the patient's head (see the red line in FIG. 3).

Figure 4:
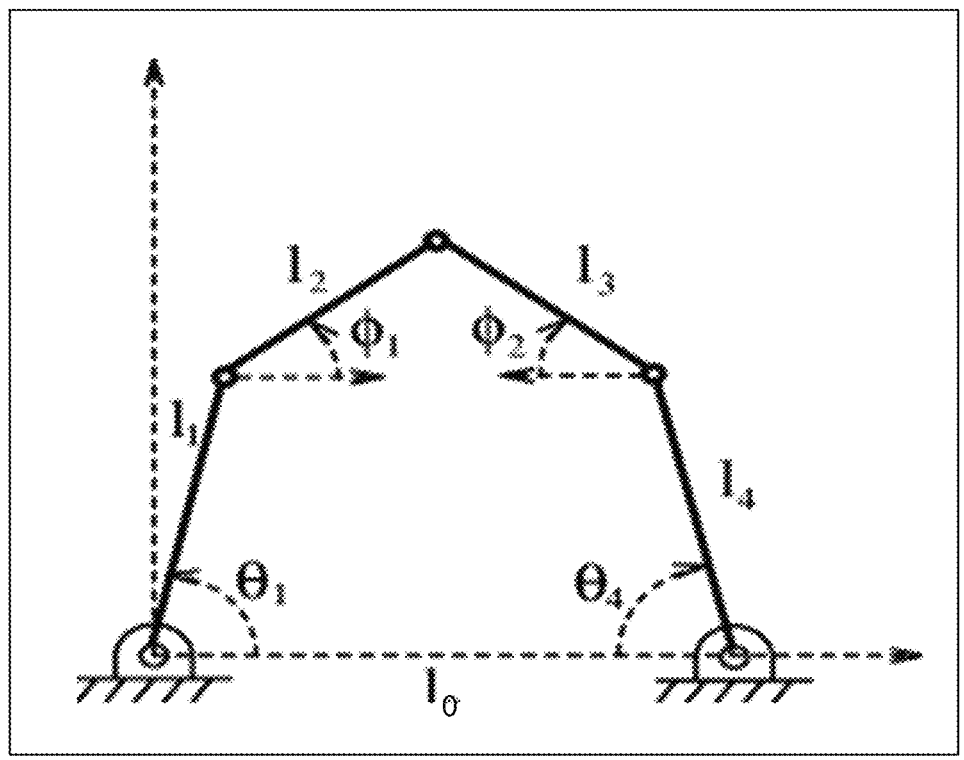
FIG. 4 shows the planar five-bar mechanism of a novel stereotactic device.

The inventors have developed a novel stereotactic device that allows the instruments to be located toward the lower part of the patient's head during robot-assisted neurosurgery. FIG. 4 shows the kinematics chain for a planar five-bar mechanism made up of links $\ell_0$ to $\ell_4$ as the basis for the novel stereotactic device. Such a closed-loop kinematics chain is composed of five links $\ell_0$ to $\ell_4$ joined by five hinges or joints, providing two degrees of freedom. If link $\ell_0$ is fixed, it can be omitted in the illustration.

Figure 5:
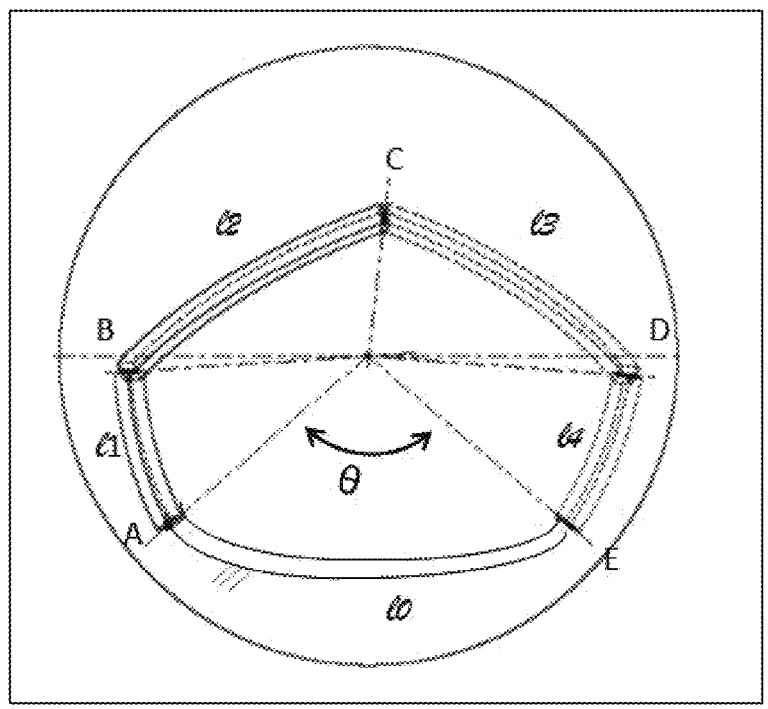
FIG. 5 shows the kinematics of FIG. 4 projected on a spherical surface.
Figure 6:
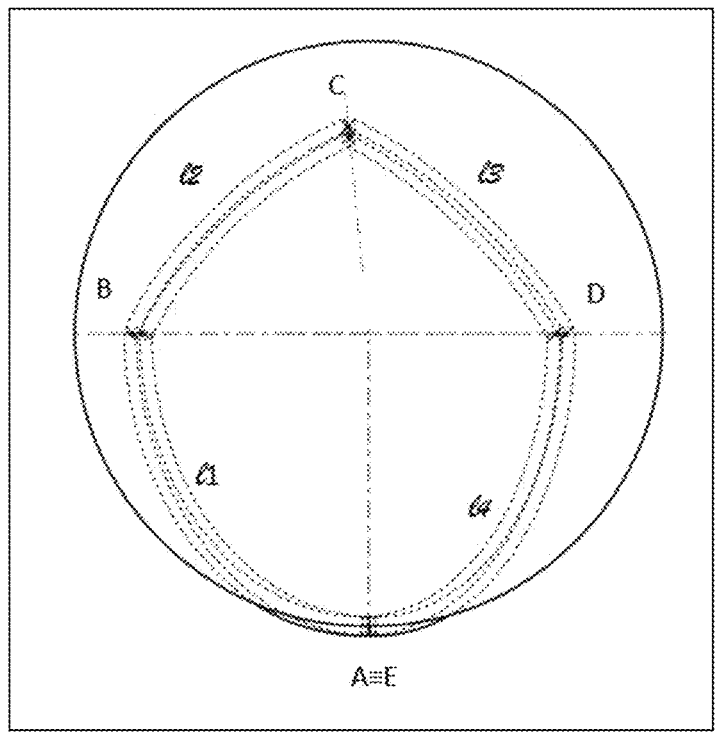
FIG. 6 shows a five-bar mechanism projected on a spherical surface.

FIG. 5 illustrates the kinematics of FIG. 4 projected on a spherical surface. The axes of joints A-E, which are parallel in the planar mechanism, are now incident to the center of the sphere. FIG. 5 also shows an angle θ between joints A and E. All the points of the links move around the spherical surface. When link $\ell_0$ is fixed, it can converge to a point. In such a case, the number of degrees of freedom does not change. FIG. 6 illustrates the spherical projection for the special (and optional) case where angle θ=0 and joints B and D are located in the diametral plane of the sphere. This results in joints/hinges A and E being located at the same point (so hinge E can be suppressed).

Figures 7A, 7B:
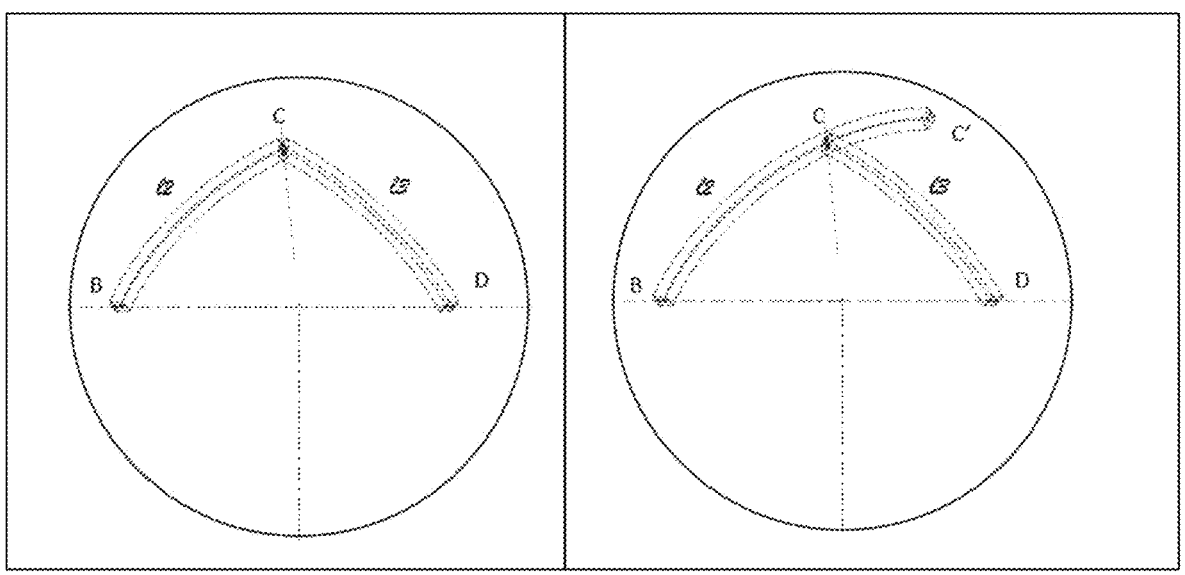
FIGS. 7A-7B show configurations of the novel stereotactic device.

FIG. 7A illustrates what happens when links $\ell_1$ and $\ell_4$ are suppressed. FIG. 7B illustrates when the end of link $\ell_2$ is optionally extended past point C to C'. The connection between $\ell_2$ and $\ell_3$, provided by a hinge, is located at the same point C, the end of link $\ell_2$ is now C'.

Figure 8:
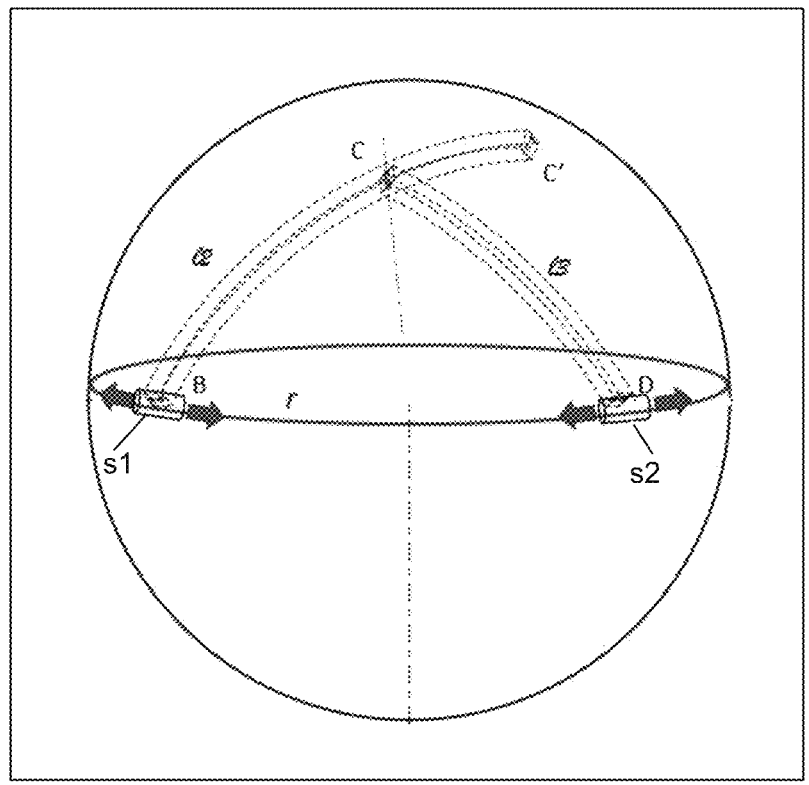
FIG. 8 shows sliders in the novel stereotactic device.

FIG. 8 illustrates the result of replacing hinged joints B and D with sliders s1 and s2 in the stereotactic device. The sliders allow independent motion of joints B and D around the diameter of the sphere. Sliders s1 and s2 may be provided with actuators if hinges B, C, and D are passive.

Figure 9A:
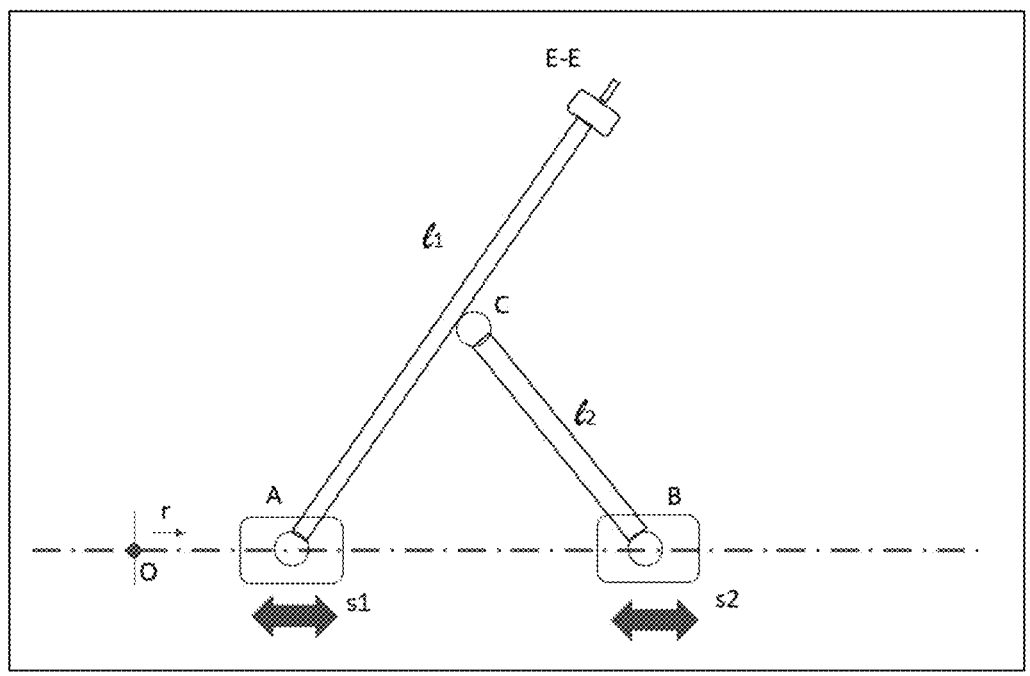
FIGS. 9A-9C illustrate an equivalent way of describing the mechanism of FIG. 8.
Figure 9B:
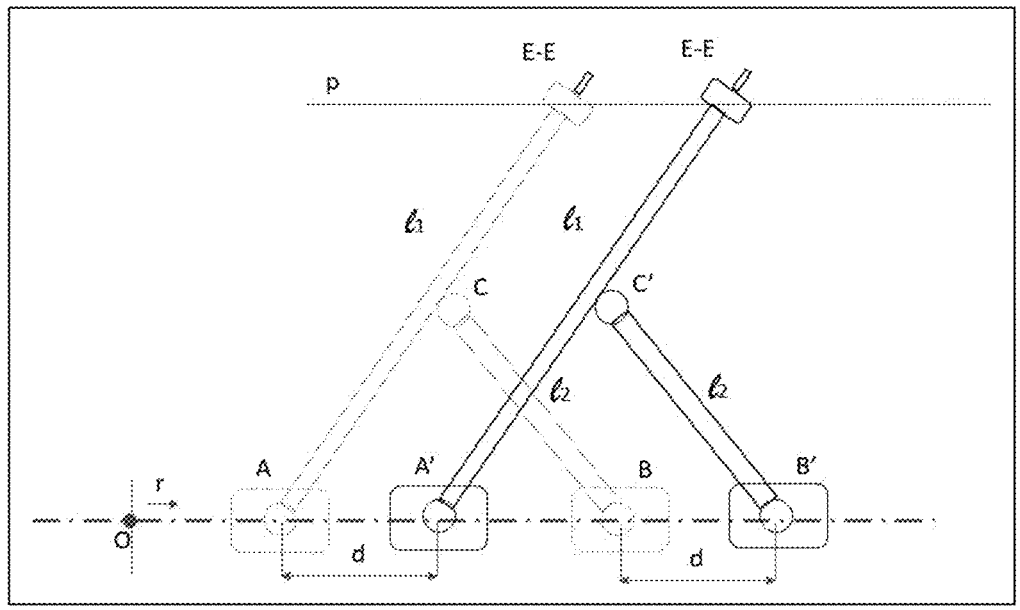
Figure 9C:
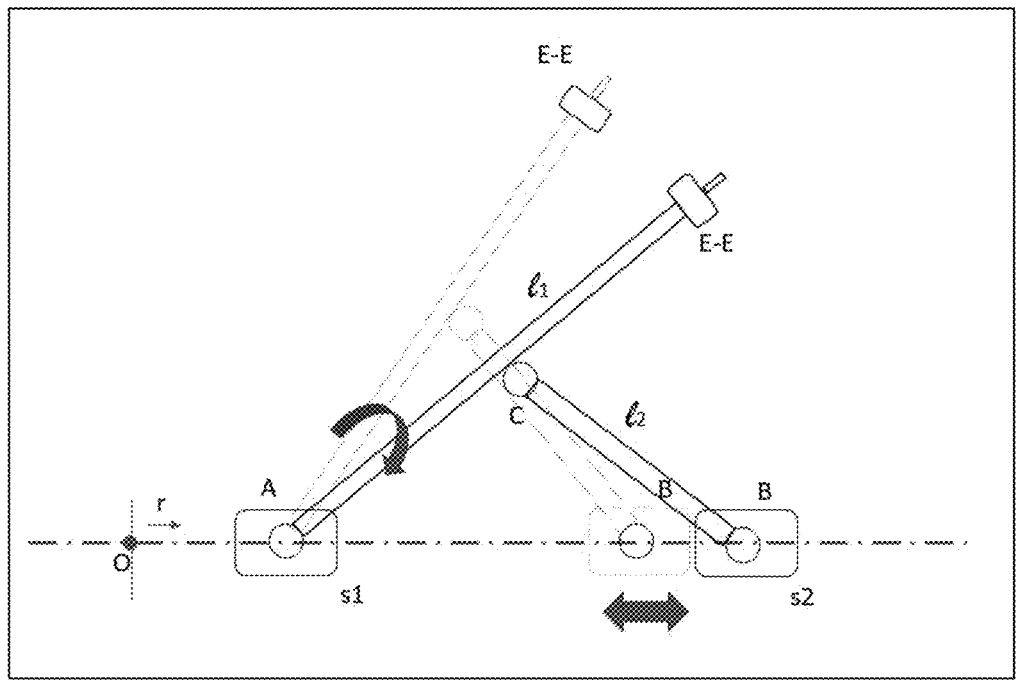

FIGS. 9A-9C illustrate an equivalent way of describing the mechanism of FIG. 8. The concept of this mechanism is based on the projection of a common planar kinematics chain on a three-dimensional surface, for example, a hemisphere. This method can be used to design a two-degree-of-freedom device moving an end effector along a spherical surface. FIG. 9A illustrates the planar kinematics for a two-degree-of-freedom mechanism. These kinematics comprise two links $\ell_1$ and $\ell_2$. Link $\ell_2$ is coupled to link $\ell_1$ by a hinge located at point C. Each link is coupled to a slider in the lower extremities at points A and B. The sliders are connected to the same horizontal axis r allowing translation. The linkage is a two degree-of-freedom chain. FIG. 9B illustrates displacement of the sliders along the r-axis by an equal distance d, moving points A, B, and C to A', B', and C', respectively. This displaces end effector E-E along an axis p (parallel to r). FIG. 9C illustrates link rotation—what happens when the sliders are displaced by different distances. When slider s2 is moved relative to slider s1, link $\ell_1$ rotates around point A. As before in FIG. 8, sliders s1 and s2 may be provided with actuators if hinges A, B, and C are passive. These figures show how end effector E-E can be moved along a plane using sliders s1 and s2. By projecting these kinematics on a spherical surface, the end effector can be moved along a sphere. This model demonstrates how two-degree-of-freedom links (e.g., a five-bar mechanism as described above) can be projected on a spherical surface.

Figure 10:
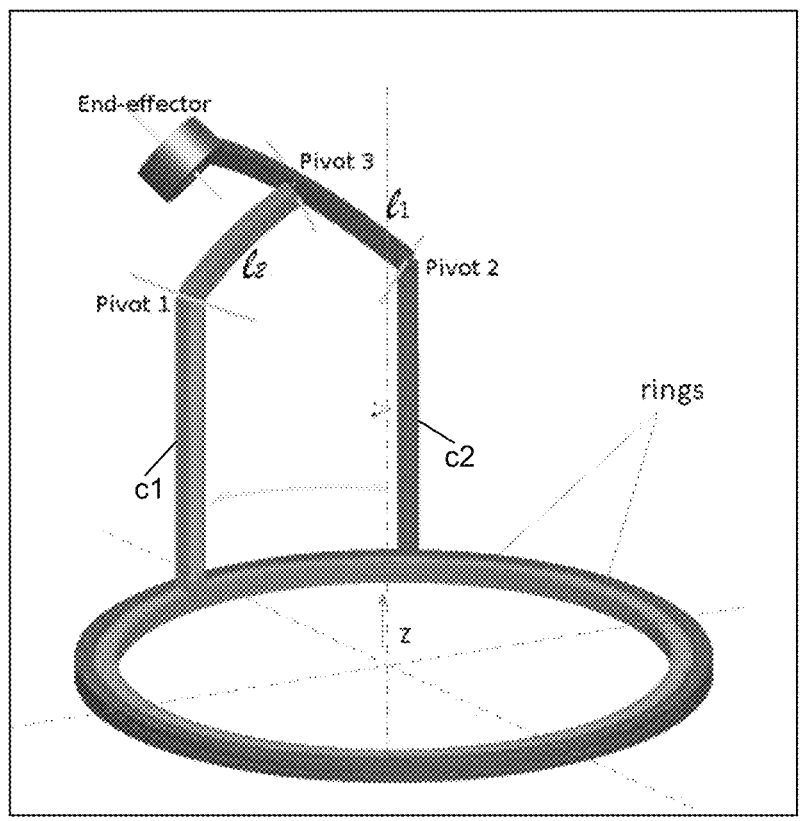
FIG. 10 shows a stereotactic device, according to an embodiment of the present invention.

FIG. 10 illustrates an embodiment of the novel stereotactic device based on the previously described kinematics. The sliders can be replaced with two coaxial and coplanar rings. A vertical rigid column, e.g., c1 or c2, may be mounted on each of the two rings. The rings may rotate independently around the common axis z. Pivot 1 is located at the top of column c1, replacing hinge D in FIG. 8. Pivot 2 is located at the top of column c2, replacing hinge B in FIG. 8. Pivot 3 replaces hinge C in FIG. 8 and allows relative rotation of links $\ell_2$ and $\ell_1$ connected to pivot 1 and pivot 2, respectively. The rotatable joints may be passive, and two actuators may be located on the base to move the rings. The two columns may be driven by actuating the rings. Rotating a single ring, the two columns get closer together (raising the end effector) or get farther from each other (lowering the end effector). If the two rings are moved together, the end-effector rotates around the head (motion along a meridian of the sphere).

Figure 11A:
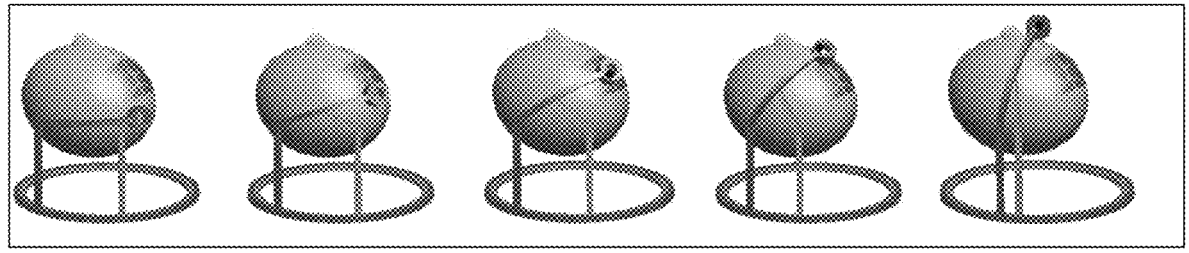
FIGS. 11A-11B show simulations of brain surgery with the stereotactic device.
Figure 11B:
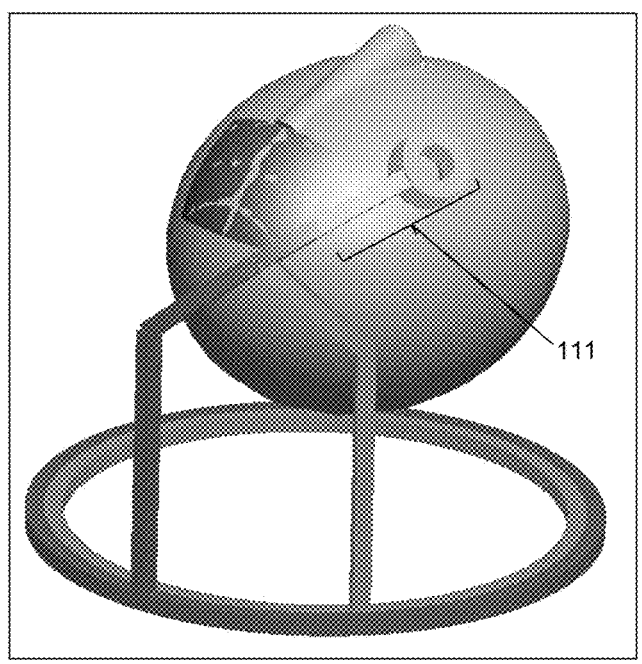

FIG. 11A illustrates a simulation of neurosurgery using the novel stereotactic device. The figure shows five different configurations of the device and the location of the end effector. FIG. 11B illustrates a simulation of an embodiment of the novel stereotactic device operating on a patient's head. Distal section 111 of the longer link may be removable and/or disposable. This allows quick replacement of the end effector or surgical instrument holder. Furthermore, this distal section may be easily disconnected for cleaning and sterilization.

Figure 12:
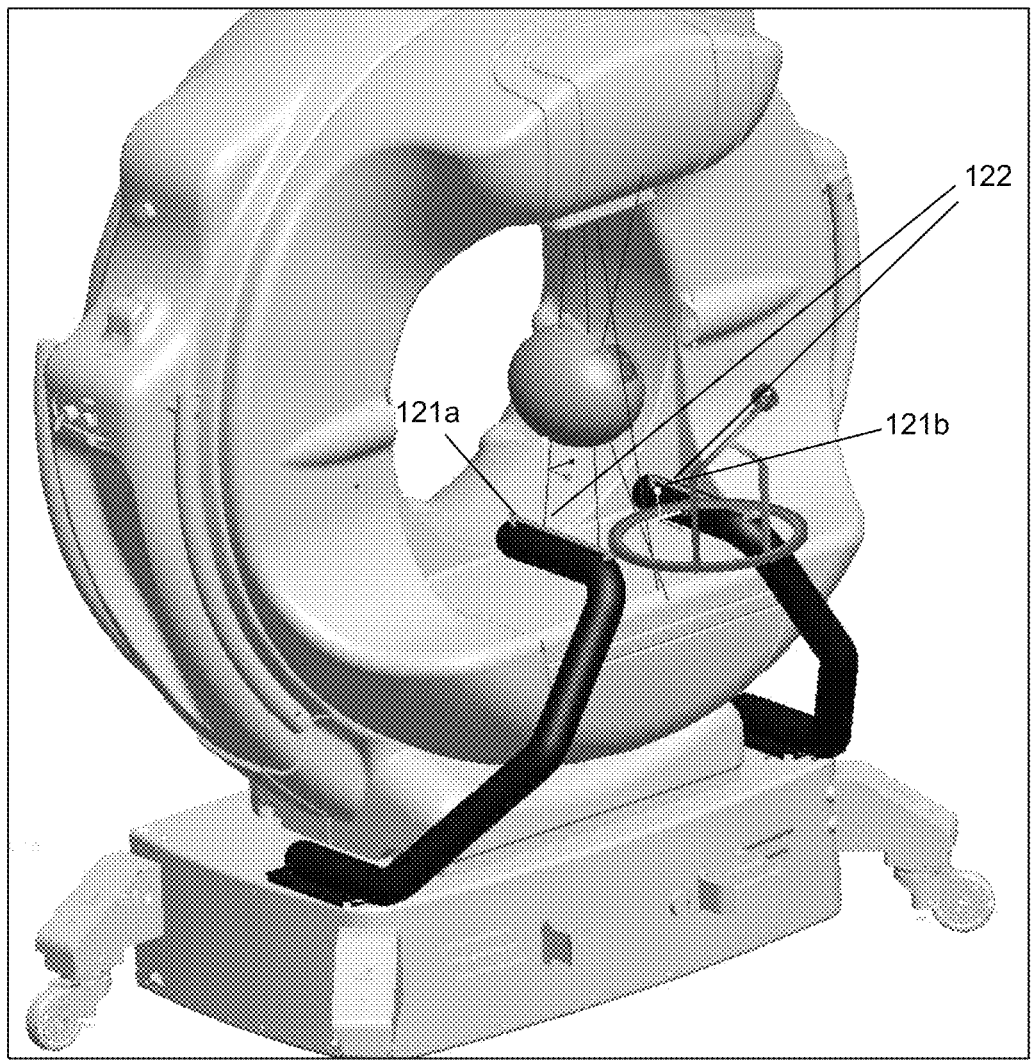
FIG. 12 shows translation of the stereotactic device.

FIG. 12 illustrates translation of the novel stereotactic device in the direction marked by lines 121a, 121b. In addition, the novel stereotactic device may be mounted on two parallel rails 122 disposed on a frame linked to a CT scanner. This feature allows the assembly to be moved away from an operating position to a rest position. The novel stereotactic device allows positioning of an end effector along a spherical (or hemispherical) surface. The end effector may be a surgical instrument holder. Generally, the surgical instrument holder holds a surgical instrument (e.g., a needle) having an axis incident to the center of the sphere (radial position). However, it is not possible to adjust the surgical instrument orientation with the two-degree-of-freedom kinematics.

Figures 13A, 13B:
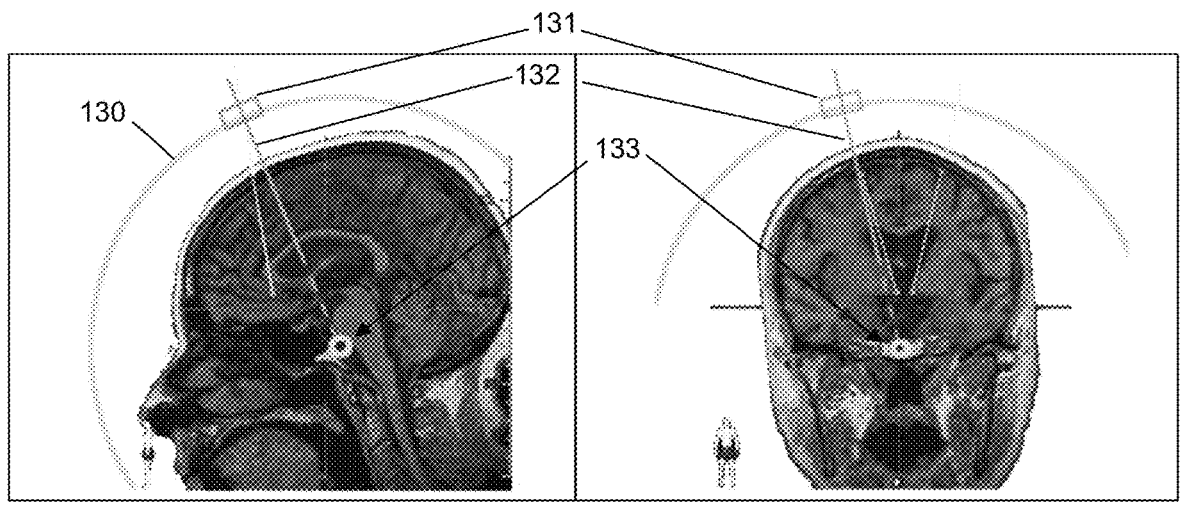
FIGS. 13A-13D show positioning and orientation of a surgical instrument during deep brain stimulation.
Figures 13C, 13D:
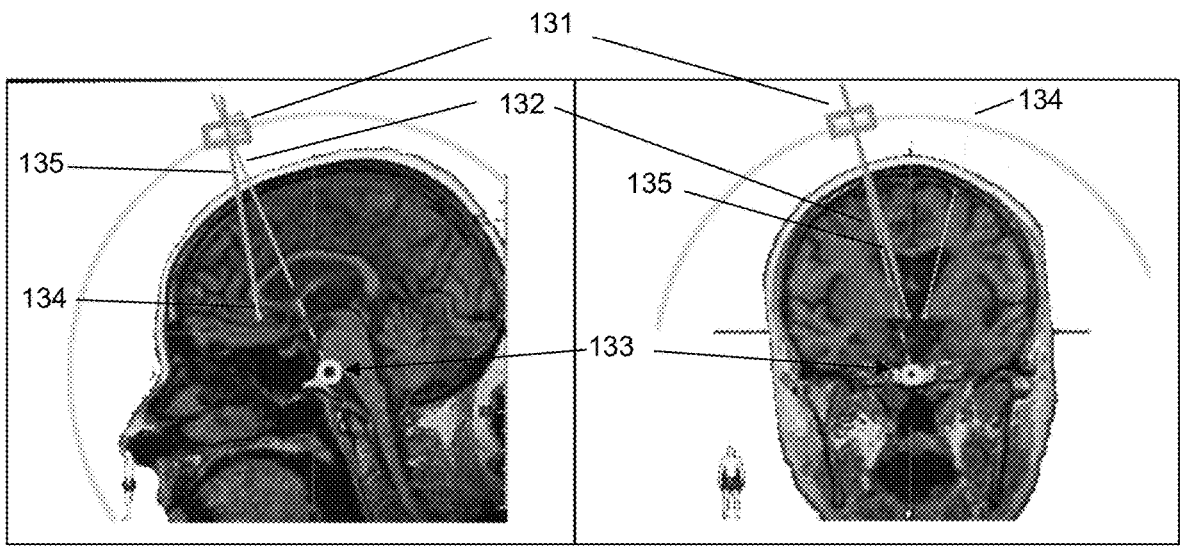

FIGS. 13A-13D illustrate positioning and orientation of a surgical instrument during deep brain stimulation (DBS). Arc 130 is the intersection between the spherical workspace and the section plane. A surgeon can move surgical instrument holder 131 along arc 130. If surgical instrument holder 131 is mounted radially, surgical instrument axis 132 points to sphere center 133 (located within the brain). FIGS. 13A and 13B show the surgical instrument positioned with no orientation adjustment. During DBS, the surgeon may need to avoid a certain area of the brain due to a possible medical complication caused by brain structure damage. In that case, depending on the point of interest, the orientation of the surgical instrument may need to be adjusted. Line 134 represents a suitable trajectory for the needle insertion. In order to follow this trajectory, surgical instrument holder 131 may be oriented along lines 135 as shown in FIGS. 13C and 13D.

Figure 14:
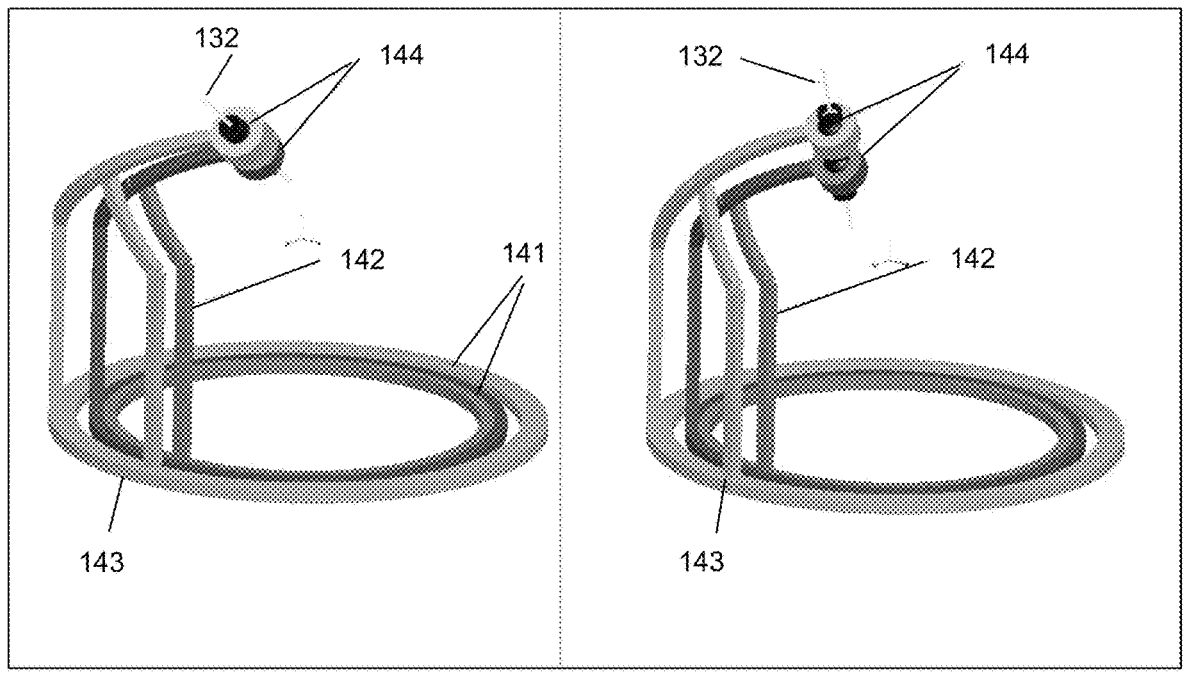
FIG. 14 shows a four-degree-of-freedom mechanism based on two coaxial stereotactic devices.

FIGS. 14-16C illustrate three systems that may be used to allow this surgical instrument orientation adjustment. FIG. 14 illustrates a four-degree-of-freedom mechanism. This mechanism couples two two-degree-of-freedom stereotactic devices having concentric rings 141 (internal ring 142 and external ring 143). The two end effectors are moved along two concentric spheres. Globally, each end effector can be positioned along a two-dimensional surface, so this system provides four degrees of freedom altogether. The extremities of the two links are connected to surgical instrument holder 131. Surgical instrument holder 131 may support spherical joints 144 that allow for the orientation of surgical instrument axis 132. These spherical joints can be moved along the two hemispheres corresponding to the stereotactic device kinematics. Surgical instrument axis 132 is incident to points of the two hemispheres. This embodiment, compared to the others described below, allows for quick repositioning and reorientation of the surgical instrument during the procedure. This can be useful to reduce a surgeon's effort and set-up time.

Figure 15:
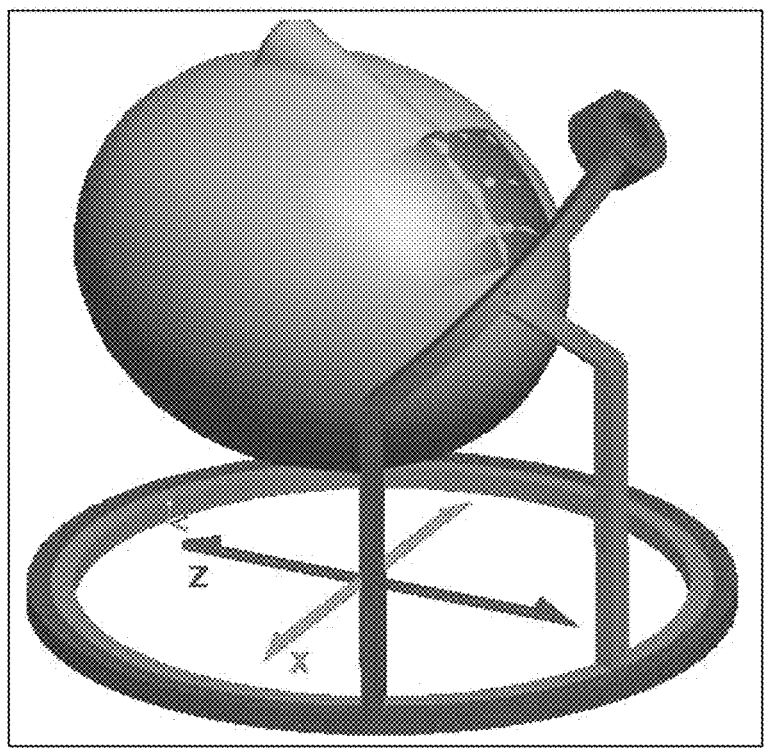
FIG. 15 shows a four-degree-of-freedom mechanism obtained by mounting a stereotactic device on a planar cartesian robot.

FIG. 15 illustrates a four-degree-of-freedom mechanism obtained by mounting a stereotactic device on a cartesian robot. Thus, this mechanism provides two more degrees of freedom than the stereotactic device. The cartesian robot can move along two planar axes x and z. Another degree of freedom (vertical translation) may also be provided. Such a configuration makes it easier to select a position at the center of the spherical workspace of the stereotactic device.

Figure 16A:
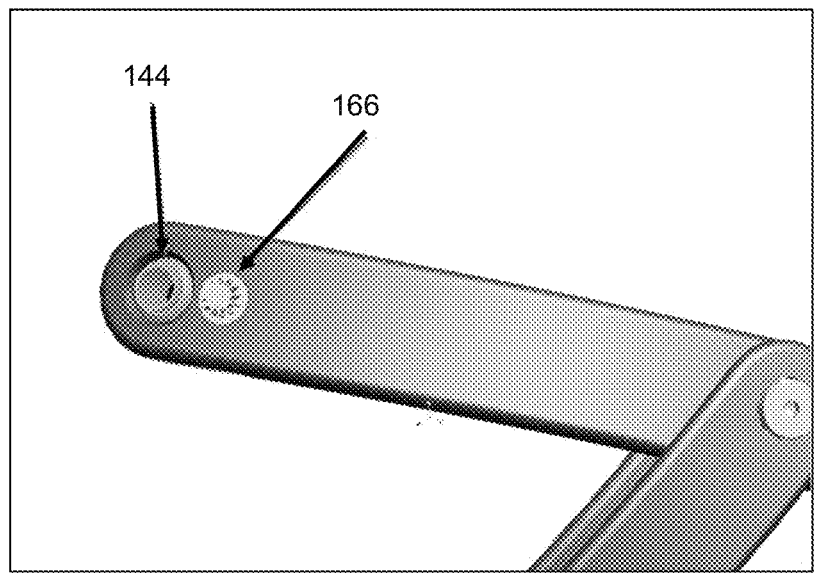
FIGS. 16A-16C show a stereotactic device having a passive arm.
Figure 16B:
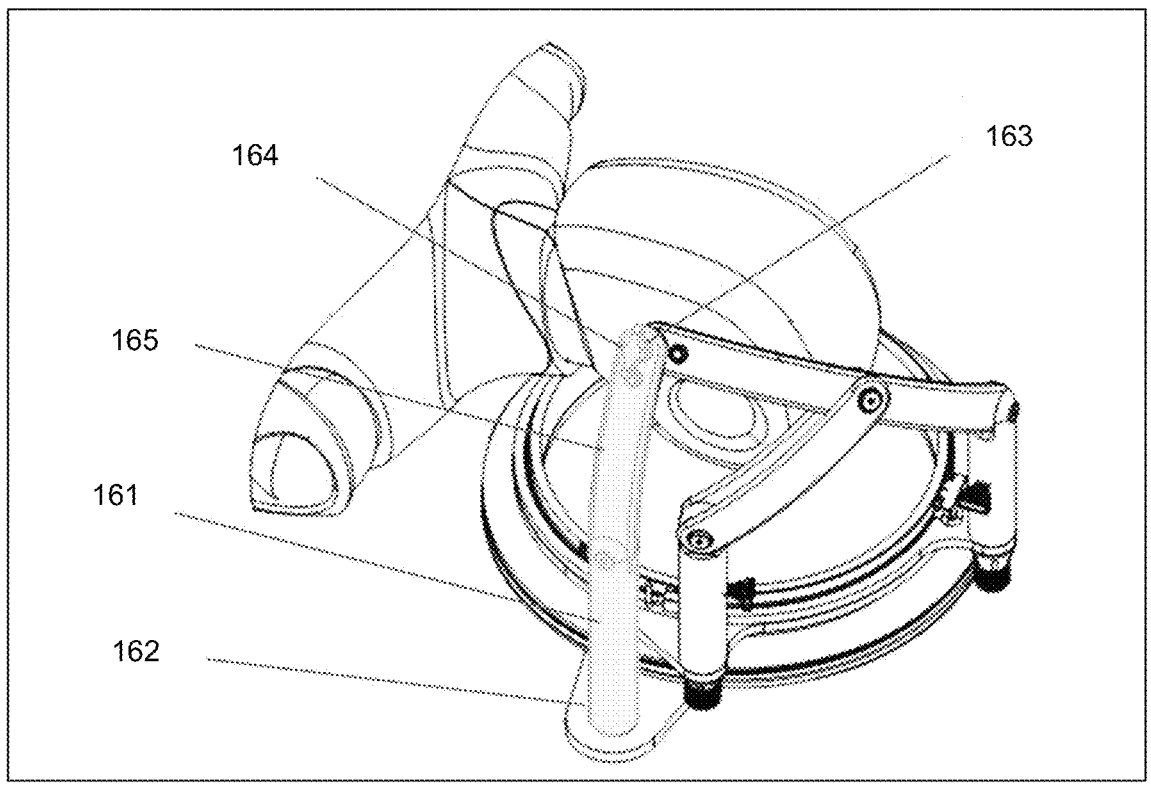
Figure 16C:
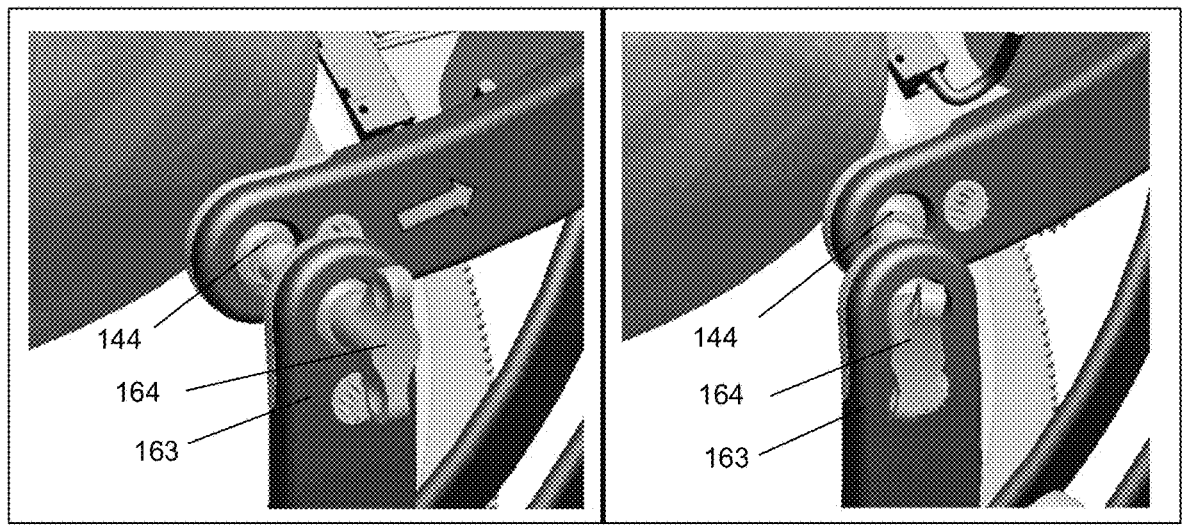

FIGS. 16A-16C illustrate the use of a stereotactic device having a passive arm. The device in FIG. 16A initially includes spherical joint 144 and locking element 166 on the end effector. Spherical joint 144 may be used to adjust the orientation of surgical instrument axis 132 (in the unlocked position). The spherical joint can be locked to maintain the selected orientation. The surgical instrument may be oriented as follows: (i) switch spherical joint 144 to the unlocked position; (ii) insert a pin (using an external robot) in spherical joint 144 to rotate it into the desired position; (iii) switch spherical joint 144 to the locked position; (iv) adjust spherical joint 144 to the proper orientation and insert surgical instrument holder 131 along the spherical joint axis; and (v) the stereotactic device locates the surgical instrument in the proper position moving in its spherical workspace. FIGS. 16B and 16C add a passive arm to the system in FIG. 16A. This passive arm can perform the task of the external robot described in the previous paragraph, resulting in a simpler system. Passive arm 161 is mounted on fixed passive arm support 162. Passive arm 161 is provided with second spherical joint 163 on its end. The stereotactic device can be moved relative to passive arm 161. The surgical instrument may be oriented as follows: (i) move the stereotactic device to locate the end effector closer to passive arm 161 (a proper relative position can be obtained using control software depending on the desired surgical instrument orientation); (ii) unlock surgical instrument spherical joint 144; (iii) insert pin 164 in the two spherical joints to properly orient surgical instrument spherical joint 144 (FIG. 16C); (iv) lock surgical instrument spherical joint 144; and (v) remove pin 164. Moreover, to make the passive arm embodiment less intrusive when not in use, passive arm 161 may include foldable end 165 (FIG. 16B), which provides a "parking position" for passive arm 161.

EXAMPLES

Figure 17A:
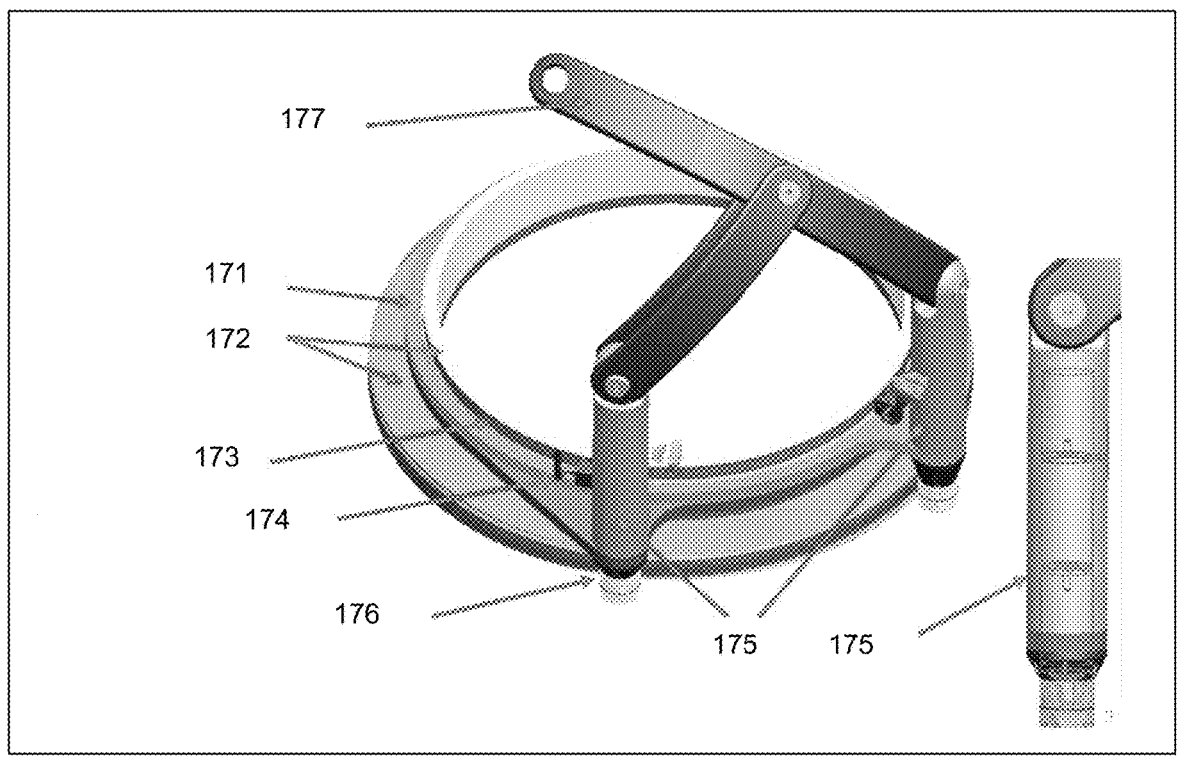
FIGS. 17A-17E show a model of a stereotactic device, along with transmission mechanisms.
Figure 17B:
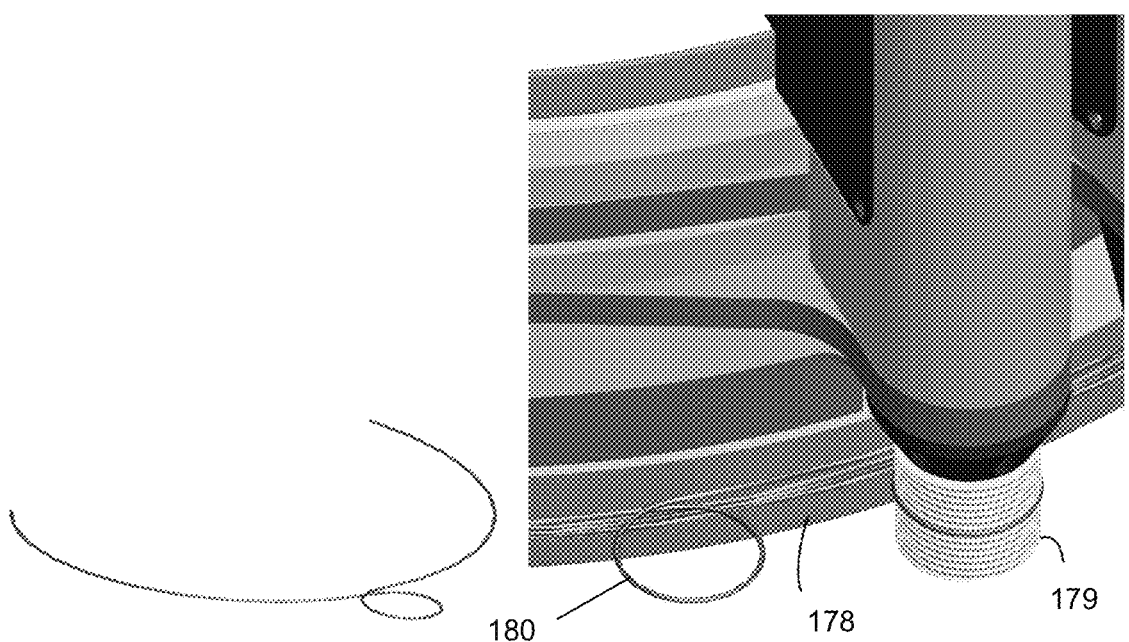
Figure 17C:
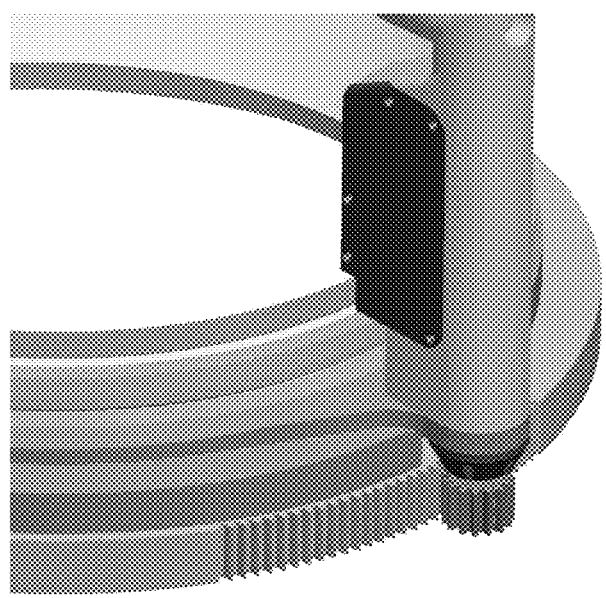
Figure 17D:
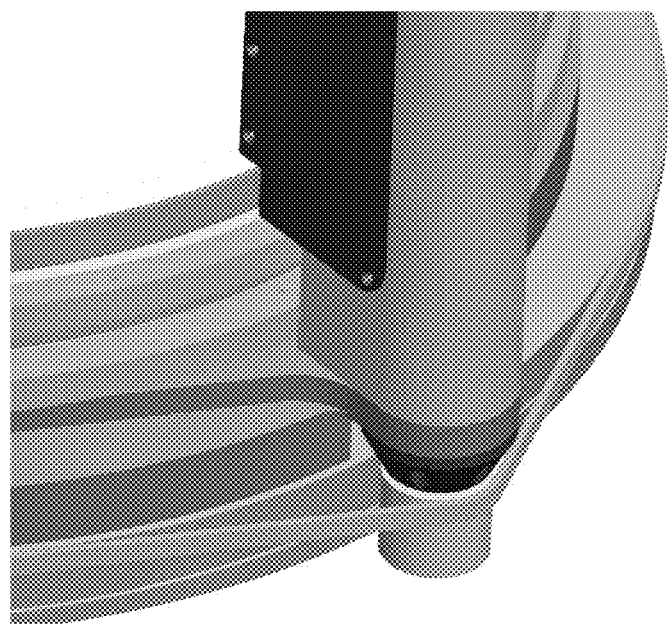
Figure 17E:
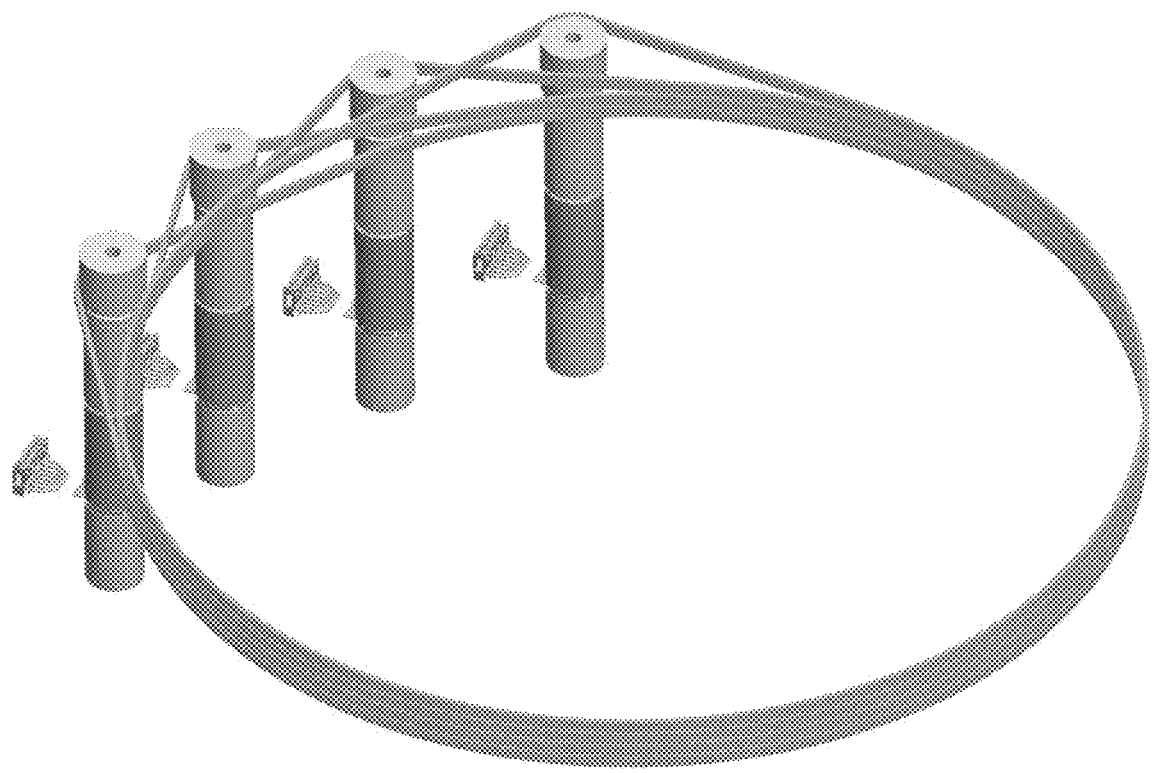

FIG. 17A shows a two degree-of-freedom stereotactic device including rotating ring 171, fixed rings 172, magnetic track 173, absolute position sensor 174, and columns 175, which include motors, gearboxes, and brakes. Rotation of the rings can be carried out by cable power transmission 176. An electric actuator can be embedded in the column (e.g., to reduce the total encumbrance and provide a wider workspace), and the driving pulley is located in the lower part of column 175 (see FIG. 17B). Removable section 177 at the end of the longer link can be disposable or removable for cleaning and sterilization. FIG. 17B shows the transmission including two pulleys (e.g., fixed pulley 178 and motor pulley 179) and cable 180 (e.g., a steel cable) having a configuration resembling an "8" to increase the contact length with the smaller pulley (e.g., motor pulley 179) and to reduce the force on the motor pulley axis. The cable terminals can be fixed on fixed pulley 178, and the power is transmitted by means of friction between cable 180 and motor pulley 179. Correct tension of the cable is required. Motor pulley 179 is fixed on the output shaft of the motor gear. In order to avoid interference, the cable can follow a spiral path on both pulleys, and these two paths can be congruent. FIG. 17C shows a pinion and annular gear, and FIG. 17D shows a transmission belt in a system based on a belt for driving the ring. Actuators can be mounted on the fixed section instead of being located within the column. One of the advantages is that motors are fixed in a stable position. This configuration reduces the global workspace of the end effector. FIG. 17E shows actuators mounted on a fixed part. Each of the four motors can move a large disk through an O-shaped belt, allowing each of four disks to rotate independently between them driven by the related motor.

Figure 18A:
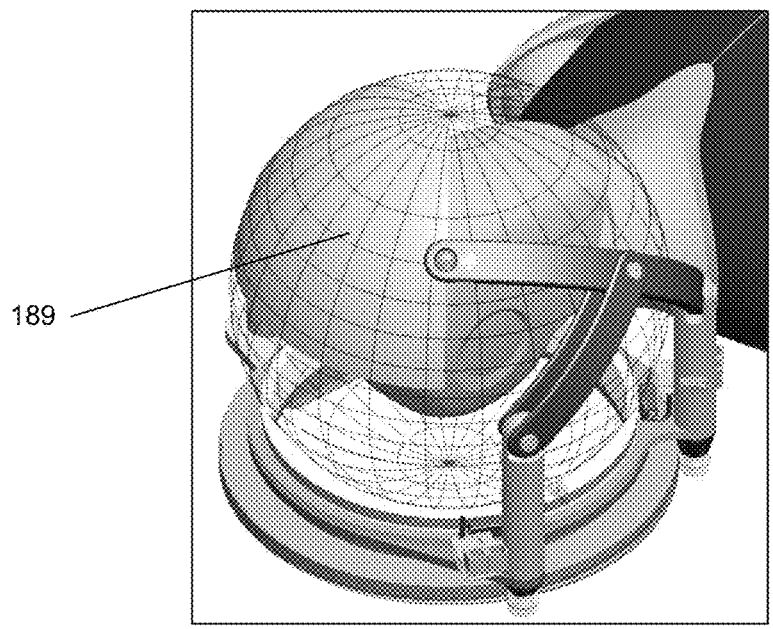
FIGS. 18A-18E show various configurations for a stereotactic device used while operating on a patient's head.
Figure 18B:
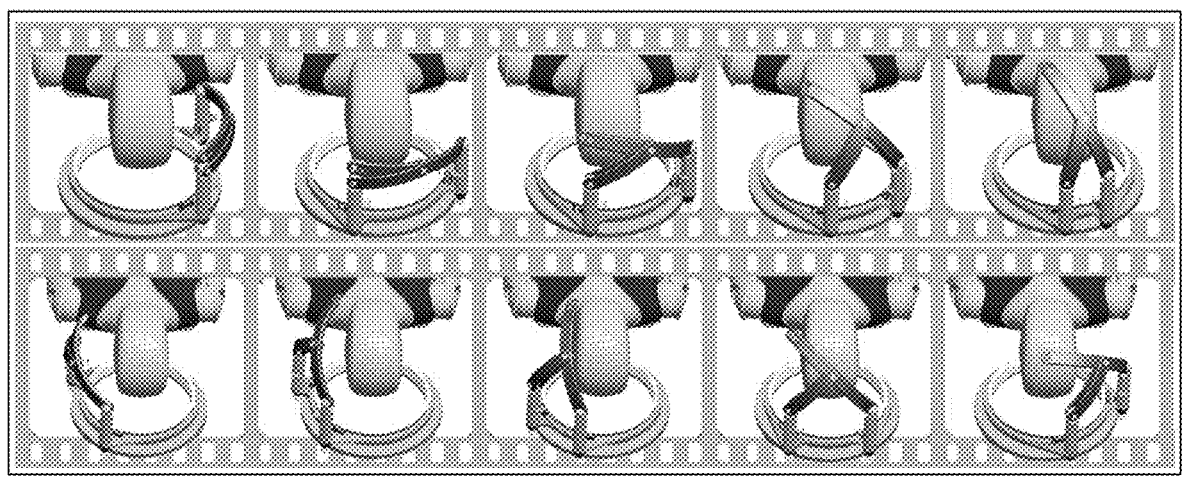
Figure 18C:
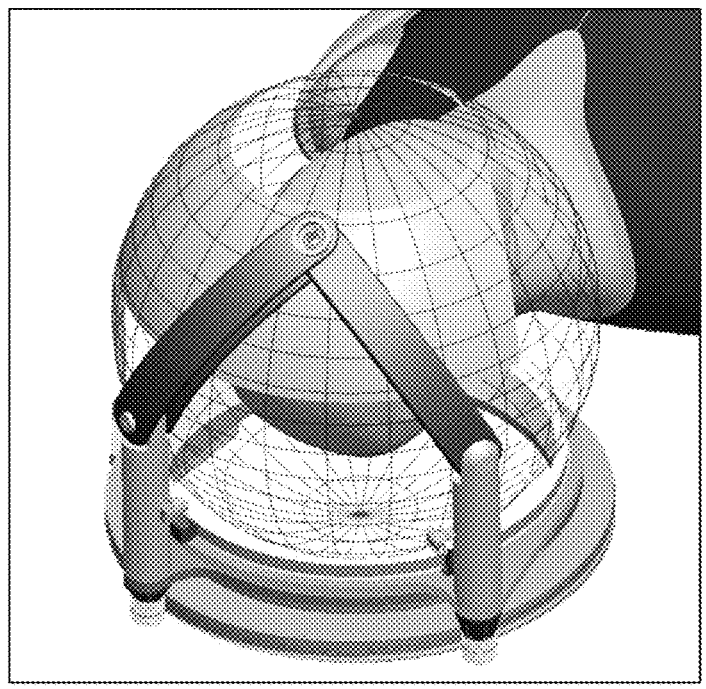
Figure 18D:
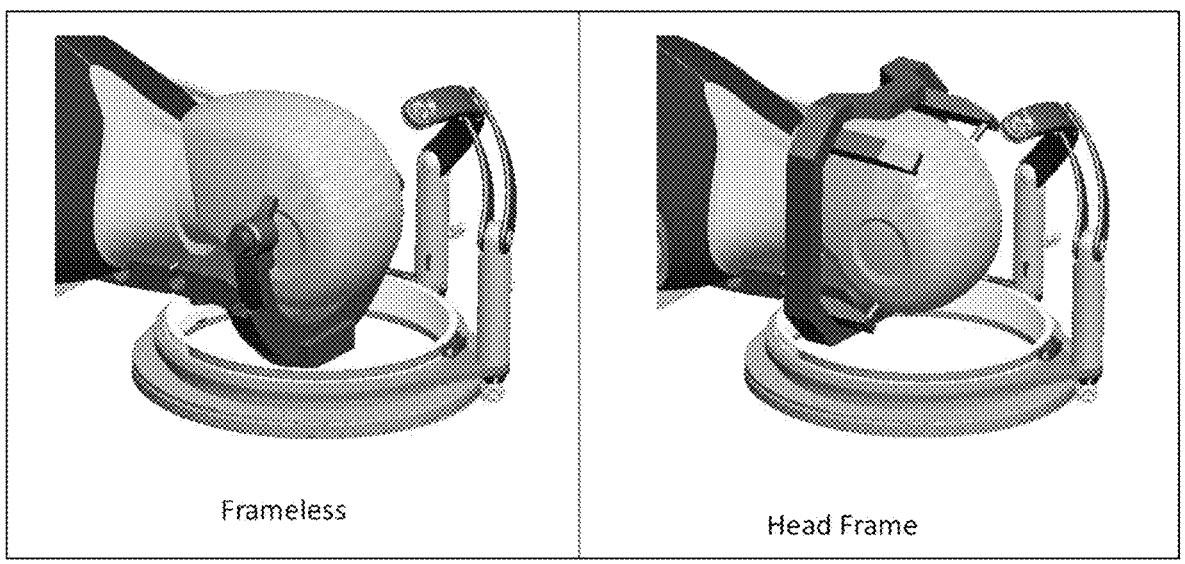
Figure 18E:
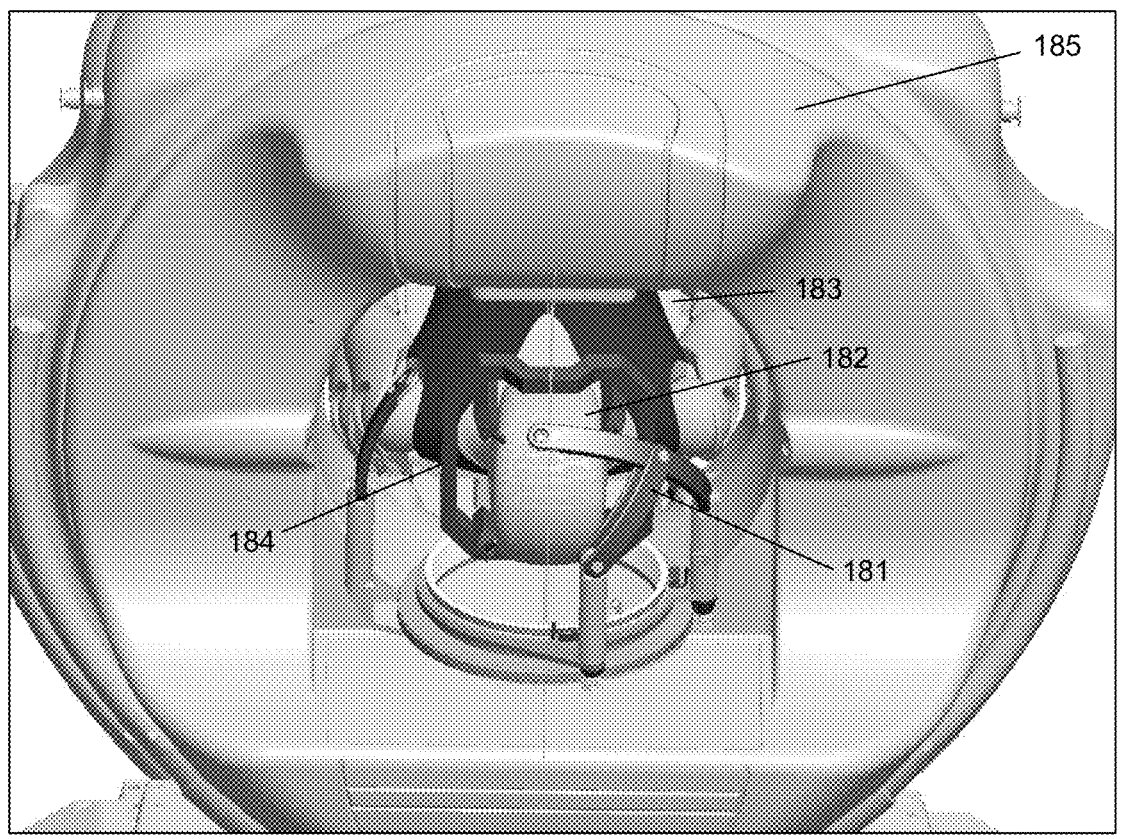

FIG. 18A shows a two-degree-of-freedom stereotactic device operating on a patient's head. The grey area 189 overlapping the patient's head model and the spherical workspace represents an estimation of the available working space (spanning area). FIG. 18B shows different positions of the two-degree-of-freedom stereotactic device operating on a patient's head. The first figure on the upper row shows the rest (parking) position that provides wide, free access to the patient's head. The workspace depends on the link configuration, in particular, the length of each link, column height, and hinge position. For example, the two links can have the same length as shown in FIG. 18C. Such a configuration provides a more symmetric workspace. FIG. 18D shows a simulation of the two-degree-of-freedom stereotactic device with a headset with or without a frame. FIG. 18E shows a system including a two-degree-of-freedom stereotactic device integrated in an imaging device. For example, stereotactic device 181 can be integrated in CT scanner 185, where patient 182, patient bed 183, and headframe 184 are positioned as shown.

Figure 19A:
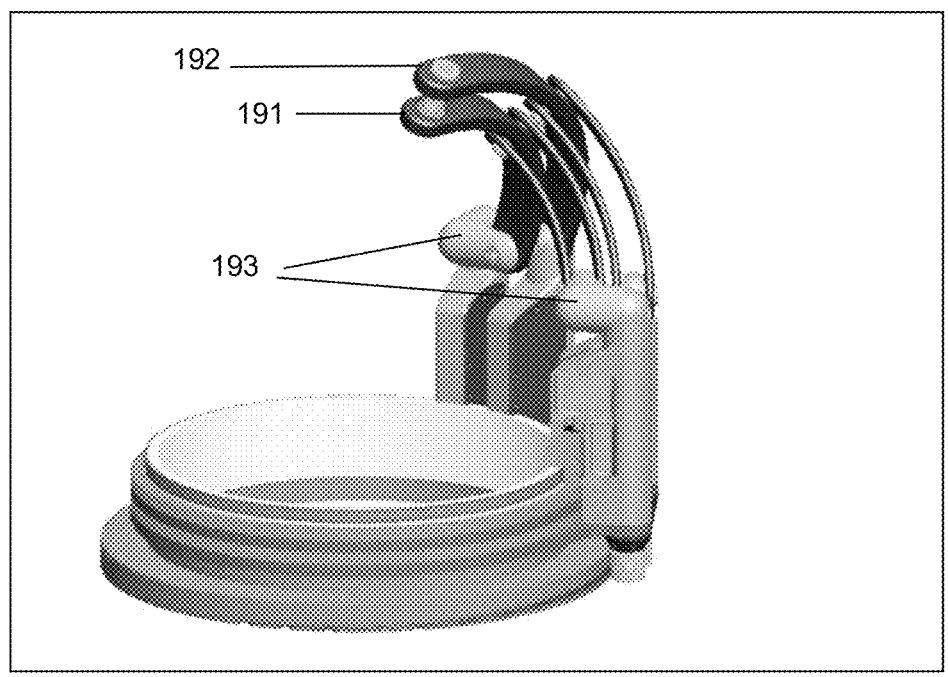
FIGS. 19A-19B show a double stereotactic device.
Figure 19B:
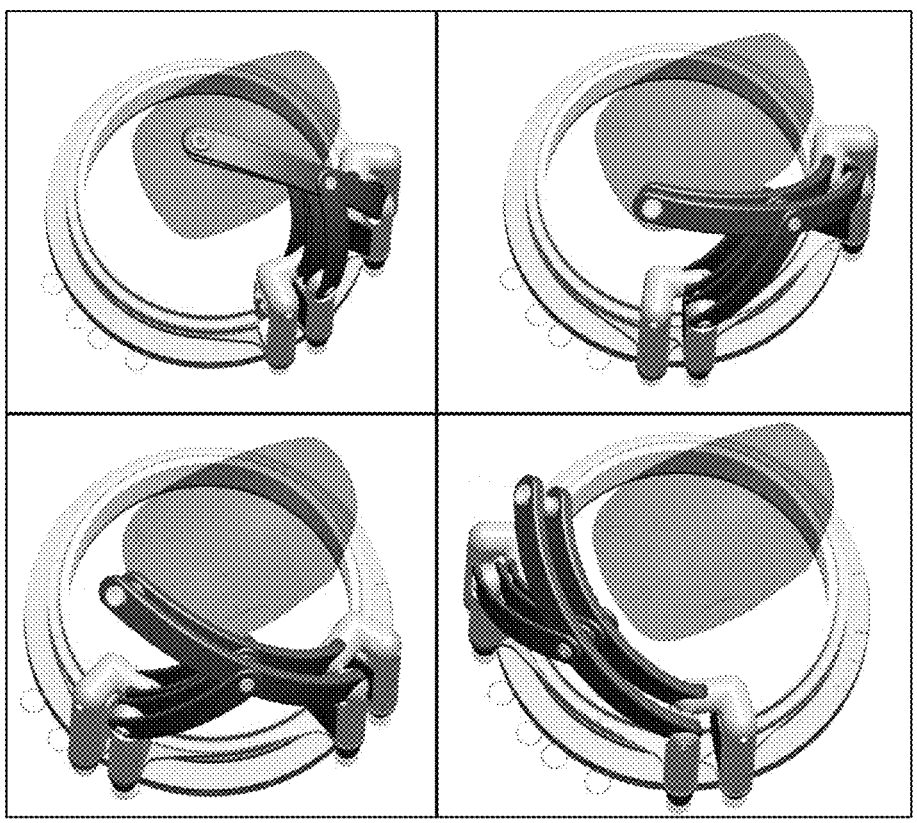

FIG. 19A shows a double stereotactic device that provides four degrees of freedom. The double stereotactic device can include two concentric two-degree-of-freedom stereotactic devices including internal frame 191 and external frame 192. Internal frame 191 can be mounted on L-shaped support 193 to reduce the global dimension and to avoid the risk of impact. FIG. 19B shows a simulation of the double stereotactic device with four different surgical instrument positions and orientations of the double stereotactic device including a patient's head.

Figure 20:
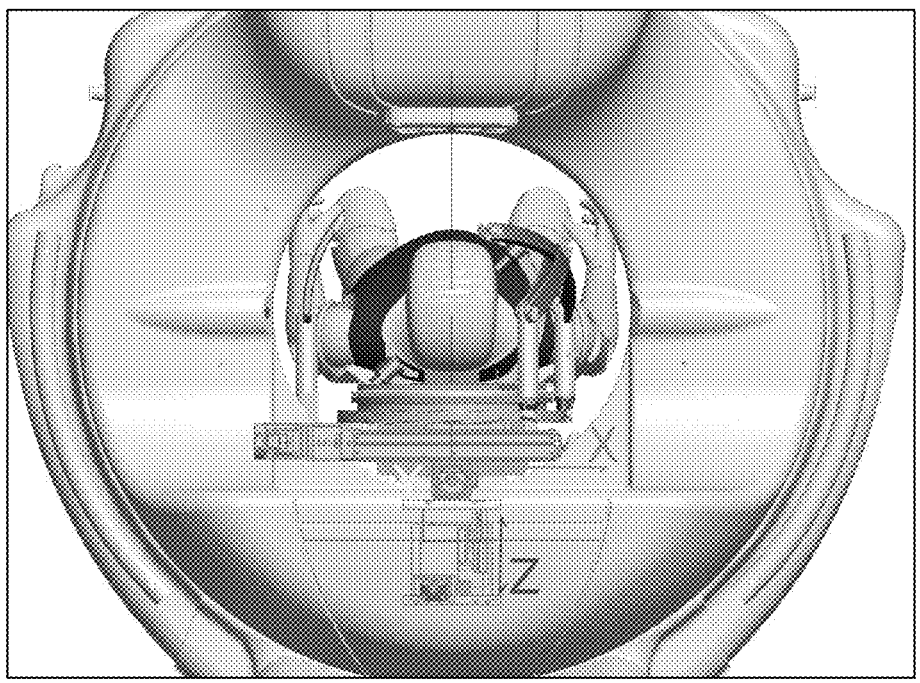
FIG. 20 shows a simulation of a stereotactic device mounted on a cartesian robot integrated with a CT scanner.

FIG. 20 shows a two degree-of-freedom stereotactic device mounted on a cartesian robot integrated with the CT scanner, as described above with respect to FIG. 15. The cartesian robot should be integrated in a manner to avoid the risk of impact to the CT gantry.

Figure 21A:
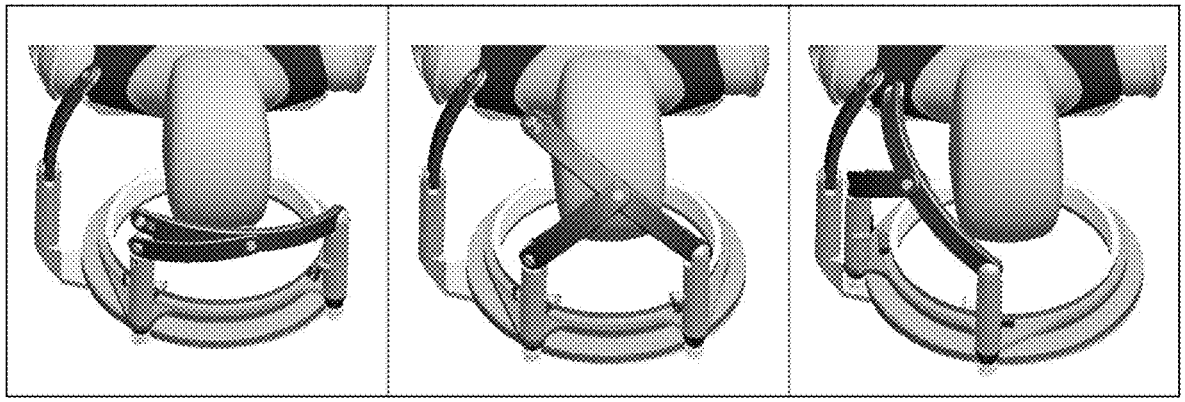
FIGS. 21A-21B shows simulations of a stereotactic device provided with a passive arm for surgical instrument orientation adjustment.
Figure 21B:
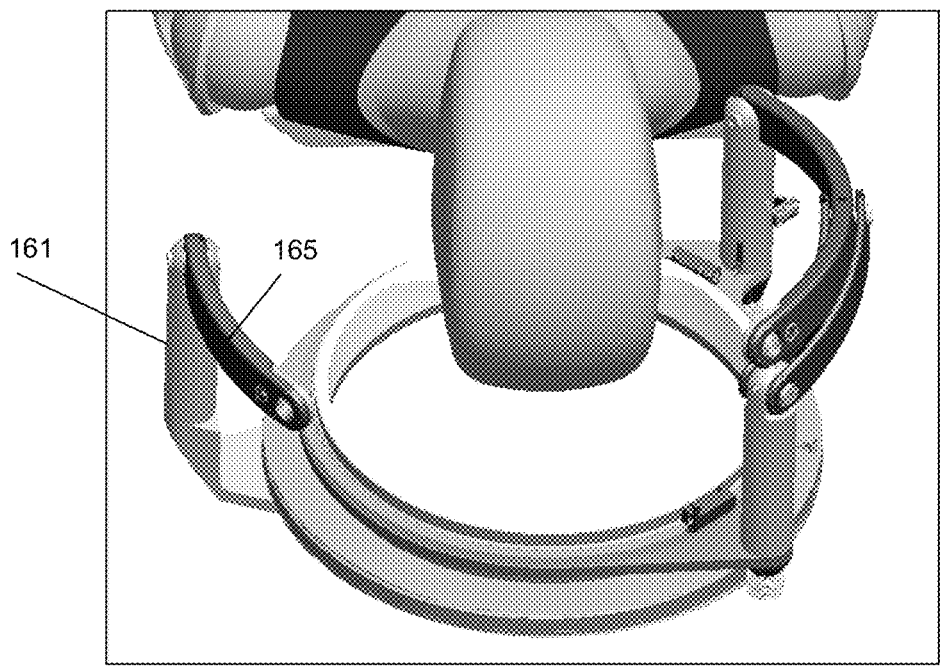

FIGS. 21A-21B show simulations of a stereotactic device provided with a passive arm for surgical instrument orientation adjustment. Foldable end 165 of passive arm 161 can be folded when the stereotactic device is in a rest position as shown in FIG. 21B.

Figure 22A:
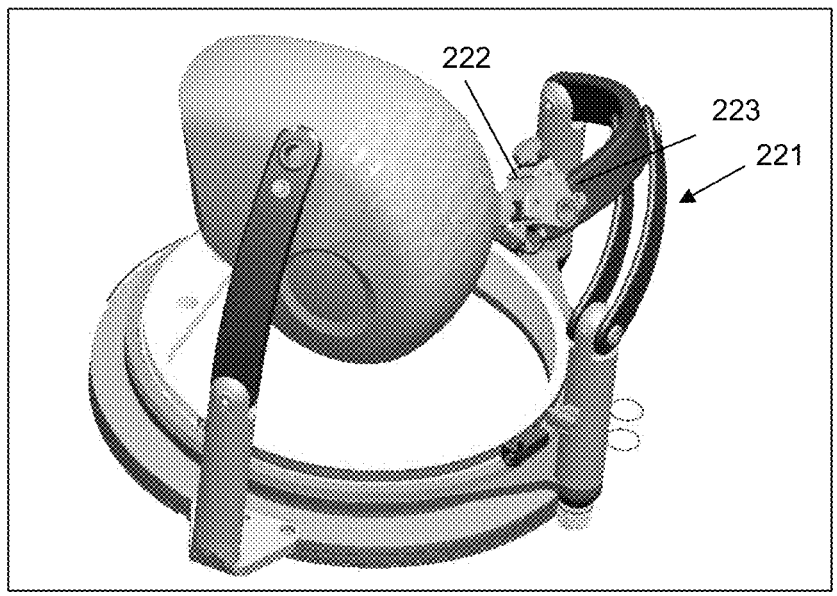
FIGS. 22A-22C show a spherical joint locking system as part of the stereotactic device.
Figure 22B:
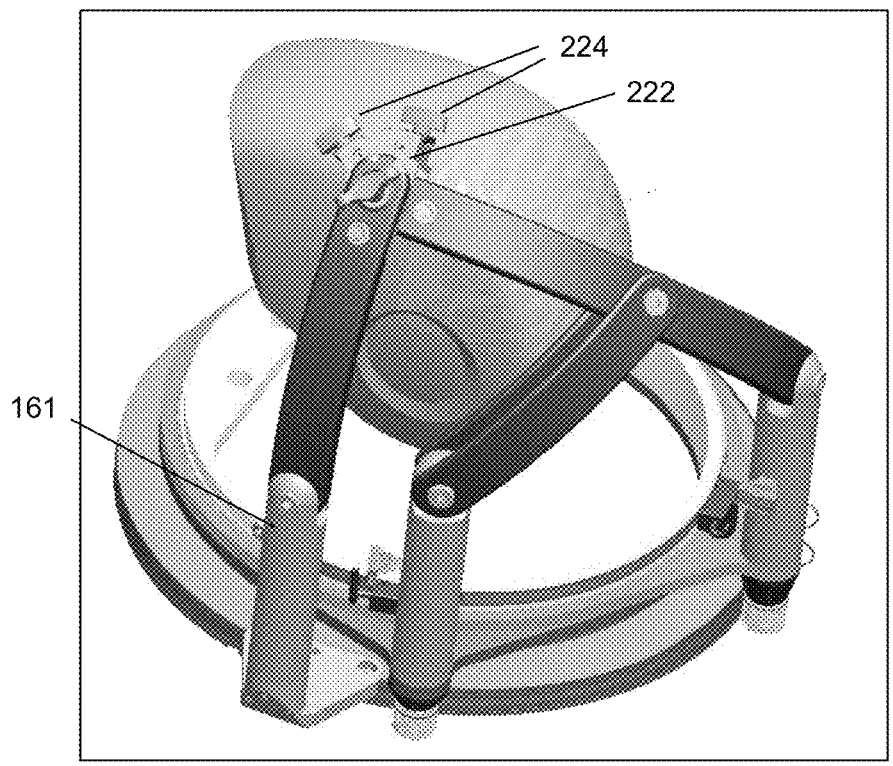
Figure 22C:
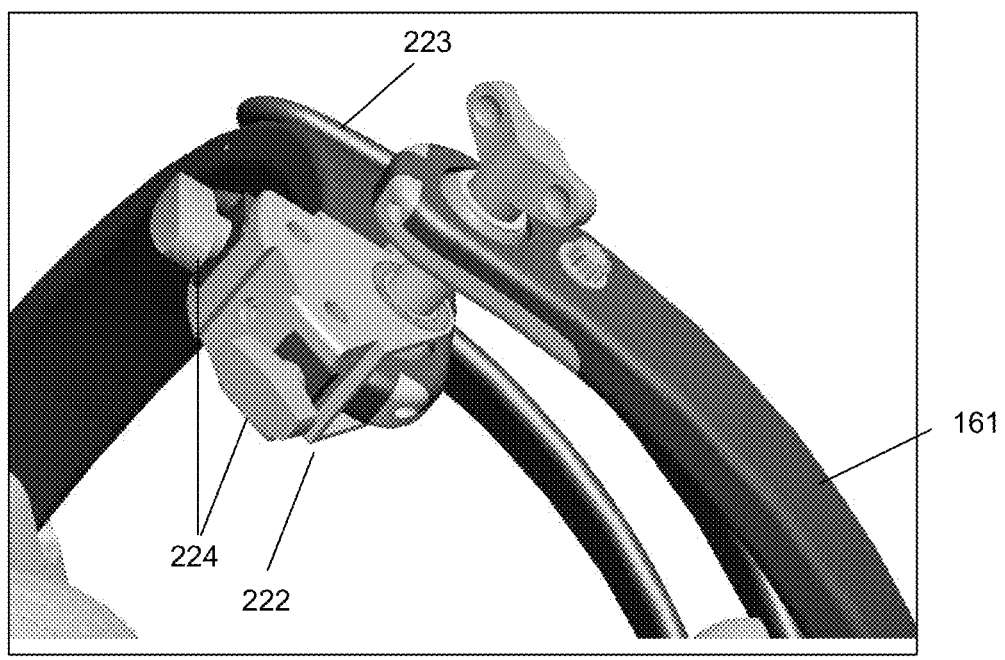

Various accessories can be included in the system. One accessory is a locking system for the spherical joint. FIG. 22A shows stereotactic device 221 provided with locking system 222 for spherical joint 223. FIG. 22B shows spherical joint locking system 222 coupled to passive arm 161. Locking system 222 includes two screws 224 acting on the joint. Screws 224 can be manually manipulatable and screws 224 can be disposed in different configurations. Locking system 222 can be integrated in an embodiment of the stereotactic device provided with passive arm 161 for the surgical instrument orientation adjustment system (see FIG. 22C for more detail).

Figure 23A:
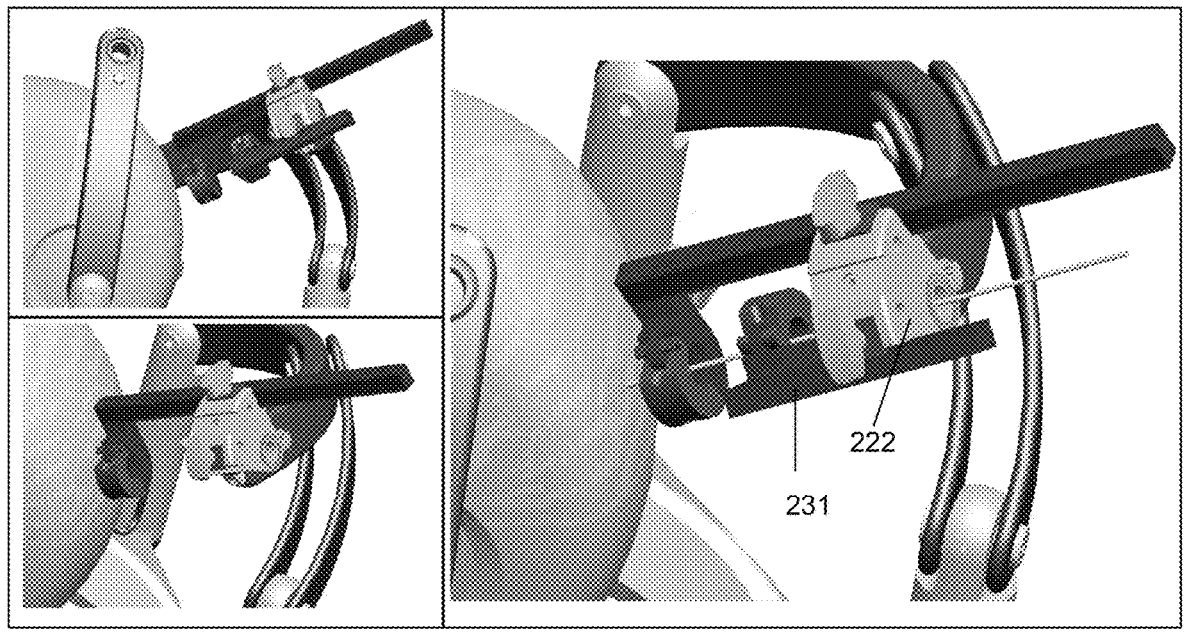
FIGS. 23A-23B show a surgical instrument holder mounted on the stereotactic device.
Figure 23B:
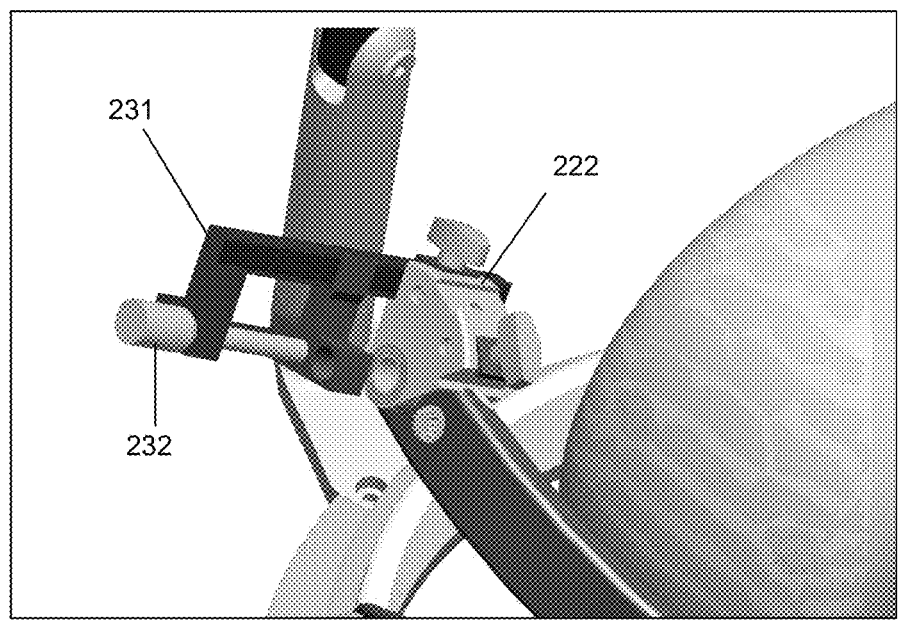

Another accessory is a surgical instrument holder integrated with the stereotactic device and locking system. FIG. 23A shows surgical instrument holder 231 mounted on the stereotactic device using locking system 222. Surgical instrument holder 231 is designed to support various commercially available surgical instruments (e.g., a microdriver) as well as customized devices. FIG. 23B shows surgical instrument holder 231 holding customized microdriver 232.

Figure 24A:
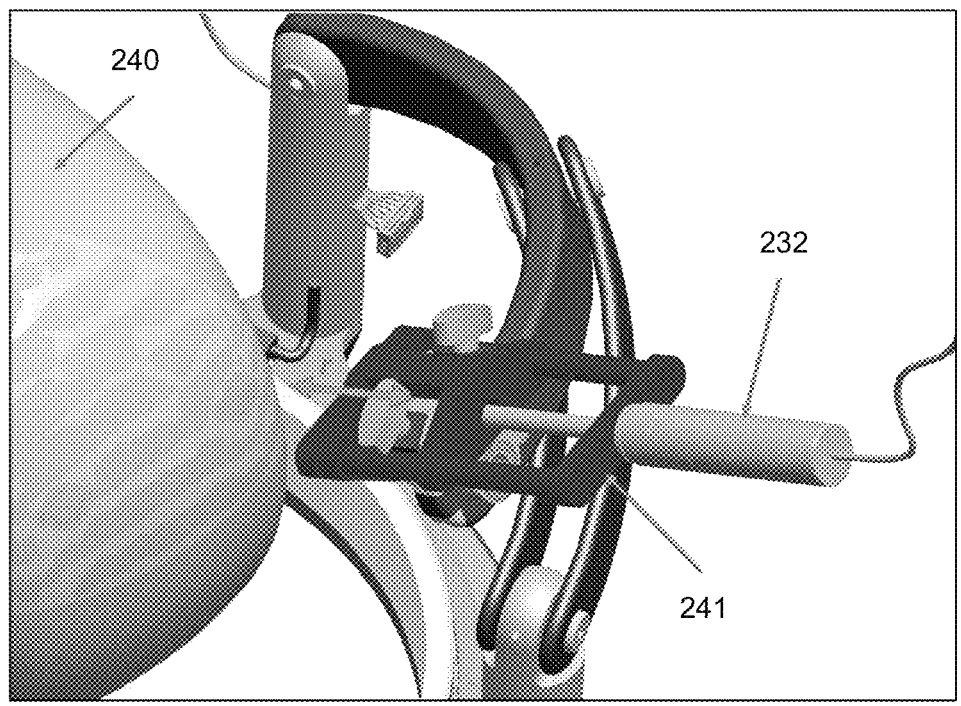
FIGS. 24A-24B show a slidable surgical instrument holder adding an auxiliary degree of freedom radially.
Figure 24B:
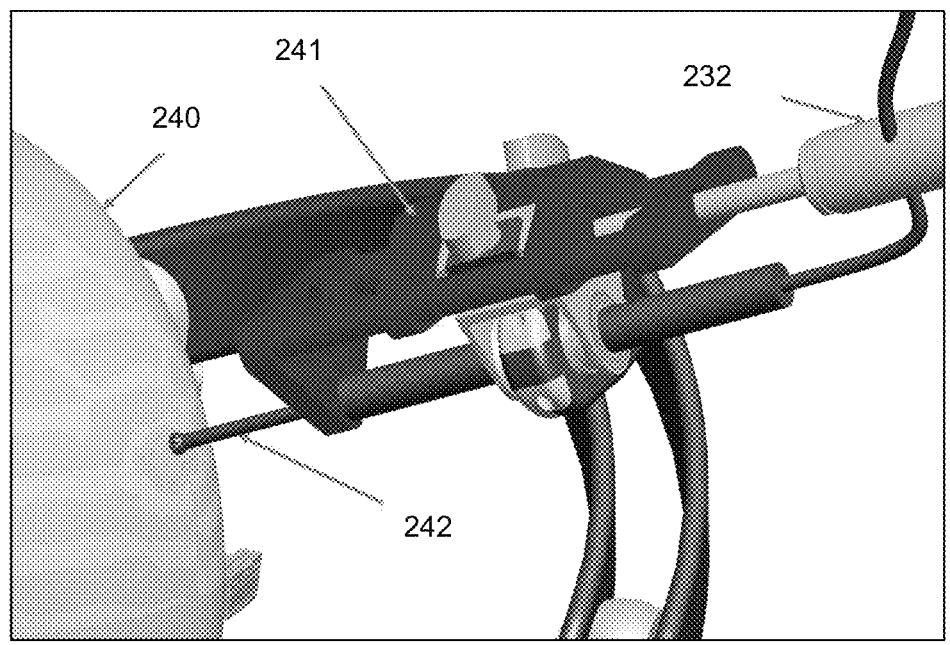

Depending on the operation to be performed, an auxiliary radial degree of freedom may be used, which permits the adjustment of the depth of the surgical instrument end in patient's head 240. FIG. 24A shows slidable surgical instrument holder 241 adding an auxiliary radial degree of freedom. Slidable surgical instrument holder 241 can be actuated and precisely adjusted by microdriver 232 along the r-axis. Such an accessory can be added to either the two-degree-of-freedom stereotactic device or the four-degree-of-freedom (double) stereotactic device. FIG. 24B shows cranial miller 242 mounted on slidable surgical instrument holder 241 (actuated by microdriver 232). Alternatively, the motor axis can be different from the surgical instrument holder axis providing a differently shaped bracket. Using a spherical mill, it is possible to perform the cranial hole drilling without making a surgical instrument orientation adjustment (within certain limits). Therefore, this system can be integrated with the two-degree-of-freedom stereotactic device having slidable surgical instrument holder 241.

Stereotactic devices so far illustrated have the rings parallel to the ground. This design works well for deep brain stimulation, but is not ideal for stereoelectroencephalography (SEEG) or hemorrhagic stroke treatment because the workspace is too small. In addition, the robot dimensions may not be compatible with a commercially available head positioning system, such as the Mayfield® positioner. For such applications, the stereotactic device may include rings perpendicular to the ground.

Figure 25A:
FIGS. 25A-25B show a stereotactic device with vertical rings installed in a CT bore.
Figure 25B:
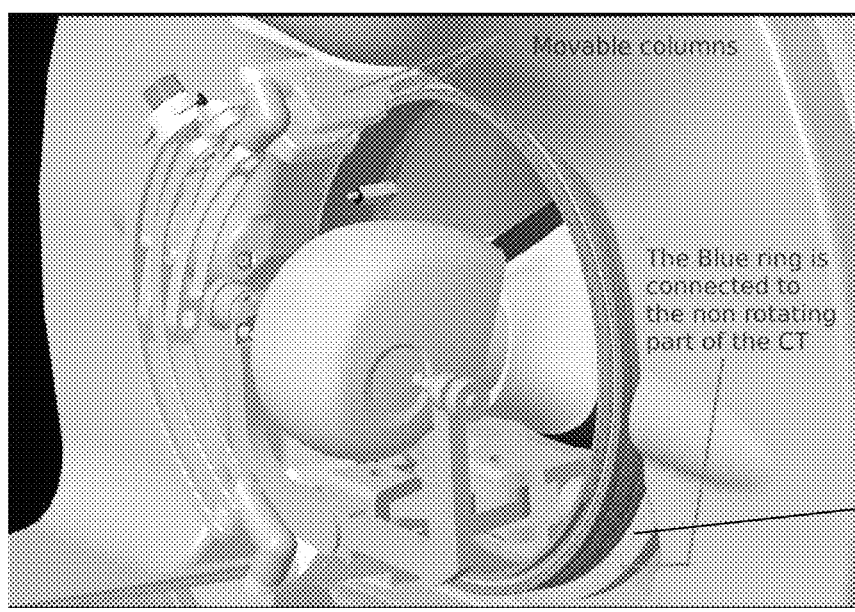

FIG. 25A shows a stereotactic device with vertical rings ("vertical stereotactic device"). This type of stereotactic device allows easy access to both the front and back areas of the skull. The stereotactic device can be installed in the CT bore and can be connected to the static part of the gantry, which provides an extended workspace. FIG. 25B shows the vertical stereotactic device installed in the CT bore. In this configuration, the stereotactic device has a section 251 that is mechanically connected to the non-rotating part of the CT. The robot is free to rotate about the CT bore with its four movable (i.e., motorized) columns, independent of the rotation of the CT gantry.

Figure 26A:
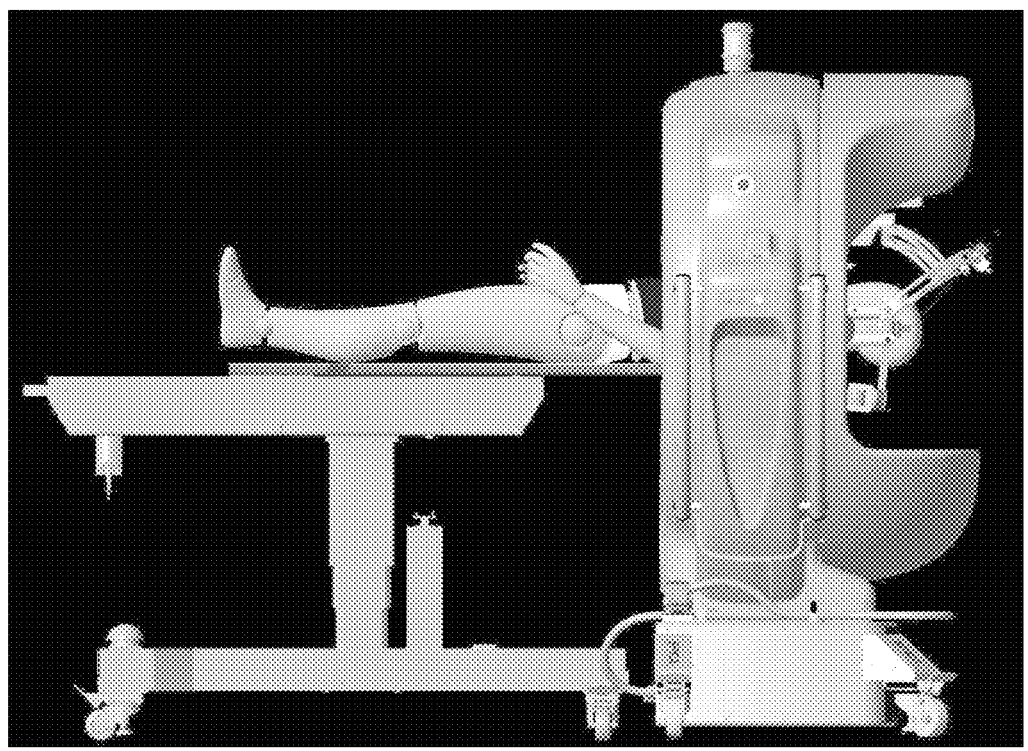
FIGS. 26A-26D show the positions of a vertical stereotactic device and the motor columns of a robot in relation to the X-ray cone area.
Figure 26B:
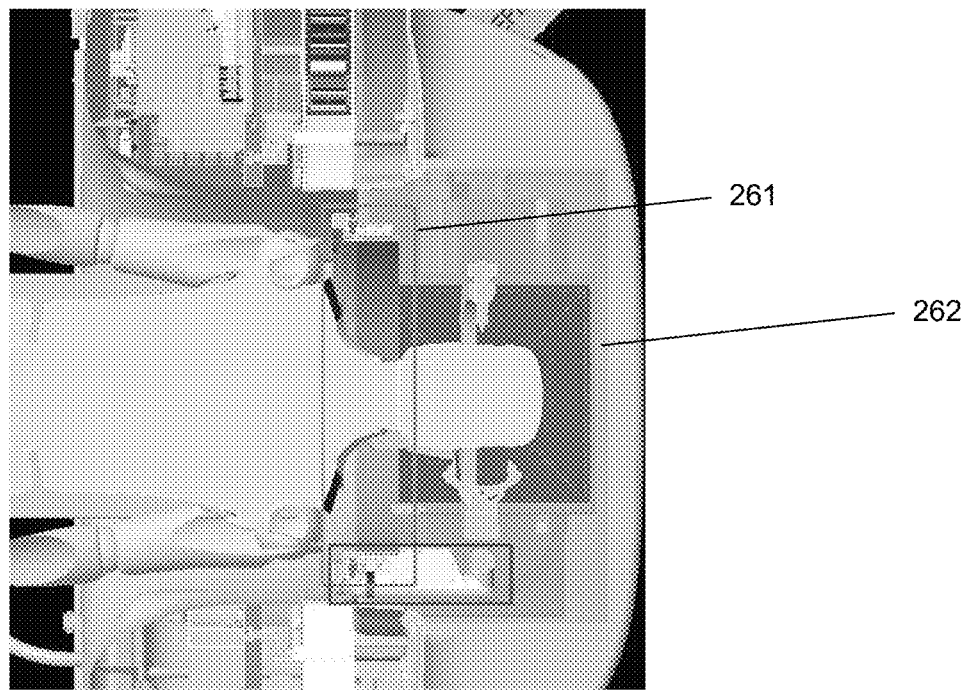
Figure 26C:
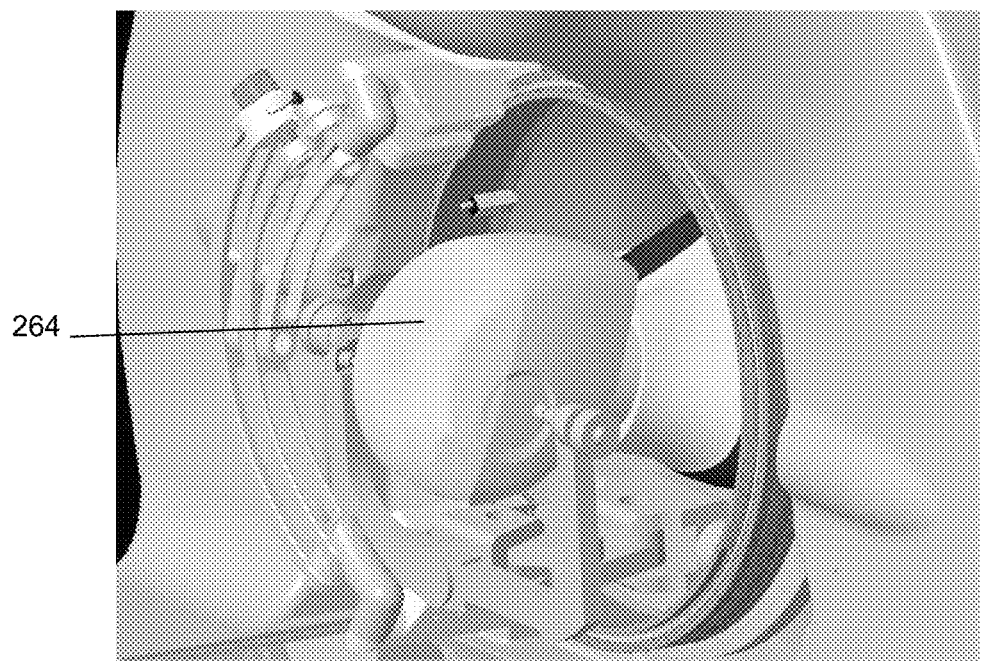
Figure 26D:
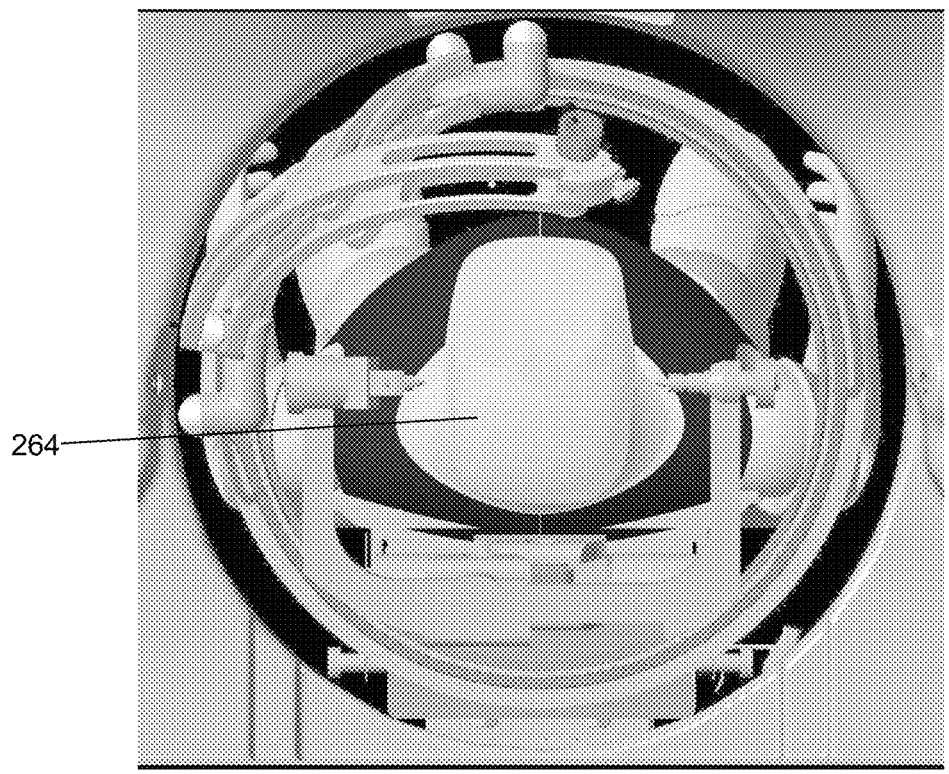
Figure 27C:
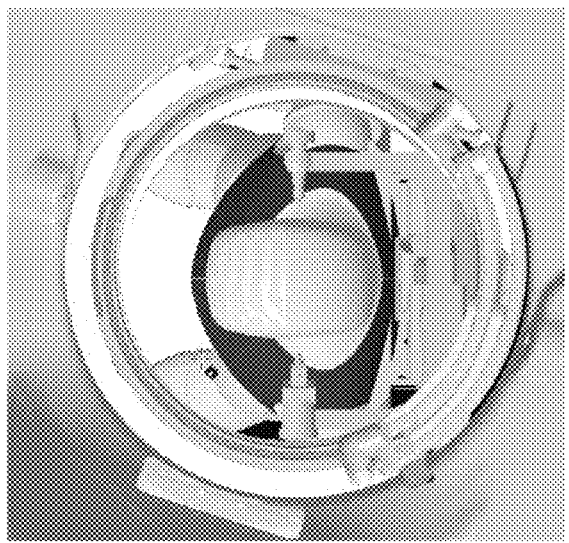
FIGS. 27A-27C show movement of the robot arm synchronized with the rotation of the CT scanner.
Figure 27B:
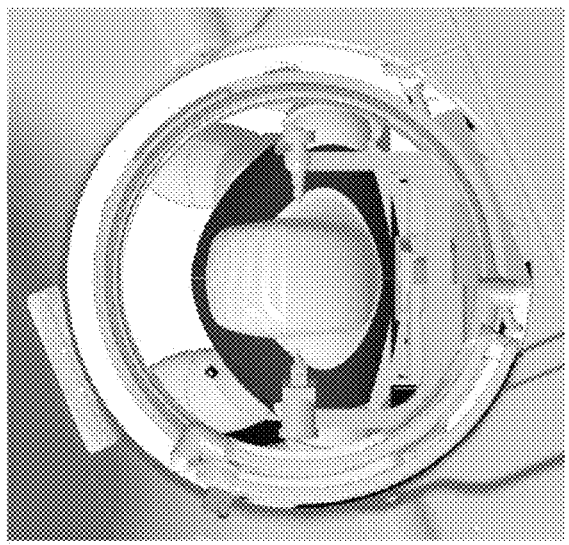
Figure 27A:
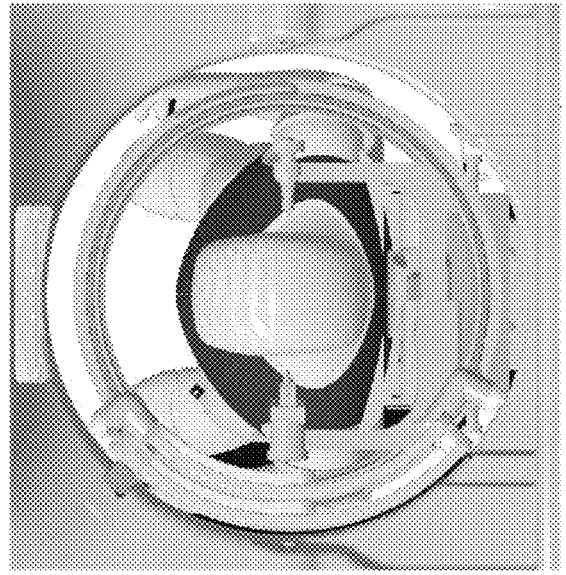

FIGS. 26A-26B show the positions of the vertical stereotactic device and the motorized columns of the robot in relation to the X-ray cone area. The red rectangle area 261 is out of the X-ray cone area (the blue square 262 under the head is the flat panel) while the robot, depending on its position relative to the X-ray source/panel axis may be within the X-ray cone. FIGS. 26C-26D show the approximate workspace provided by the vertical stereotactic device in area 264 on the patient's head. FIGS. 27A-27C show the movement of the robot arm synchronized with the rotation of the CT. This may improve the chances that the robotic arm stays out of the x-ray cone.

Figure 28A:
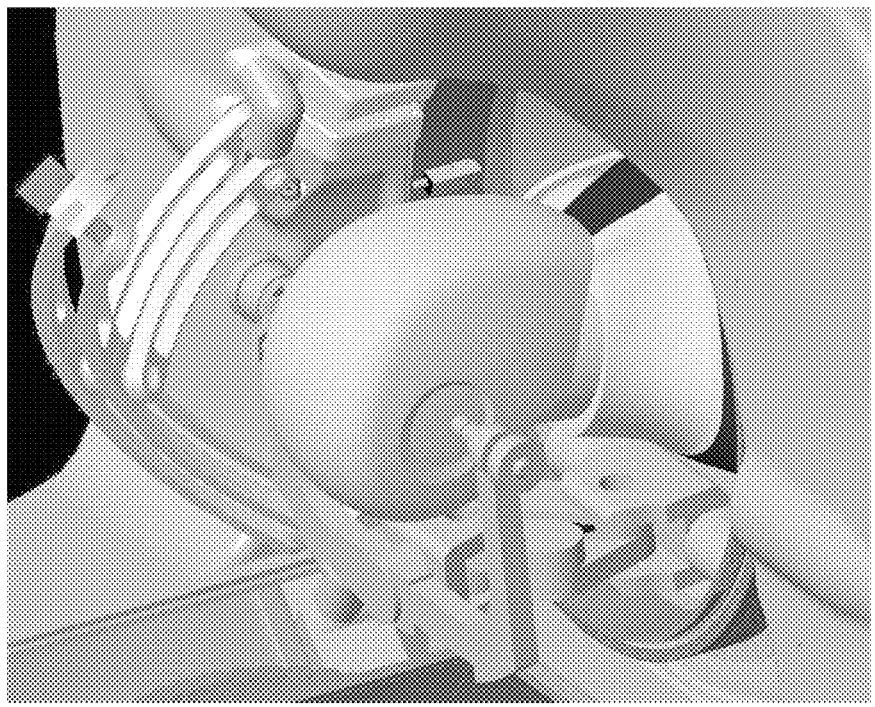
FIGS. 28A-28B show a modification of the links holding the end effector.
Figure 28B:
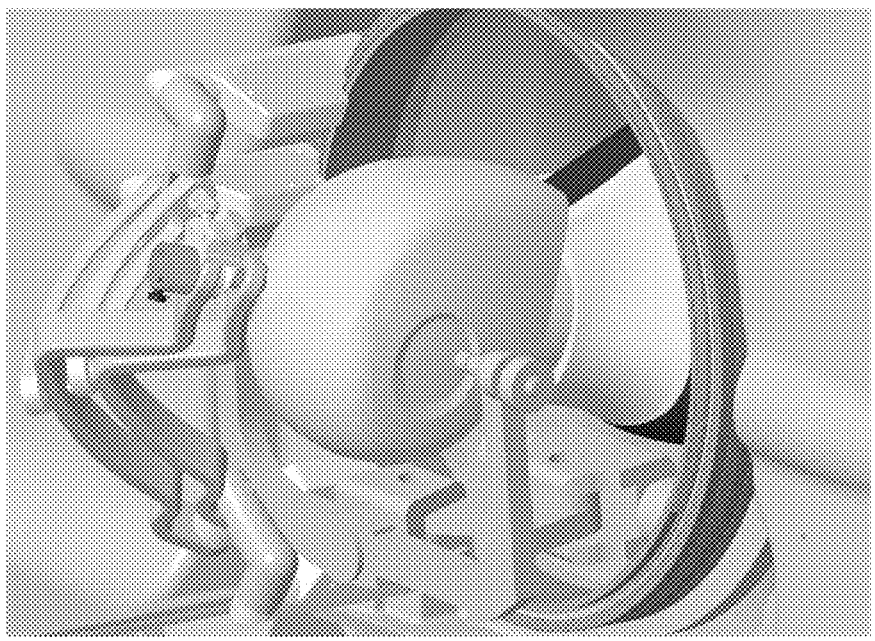
Figure 29A:
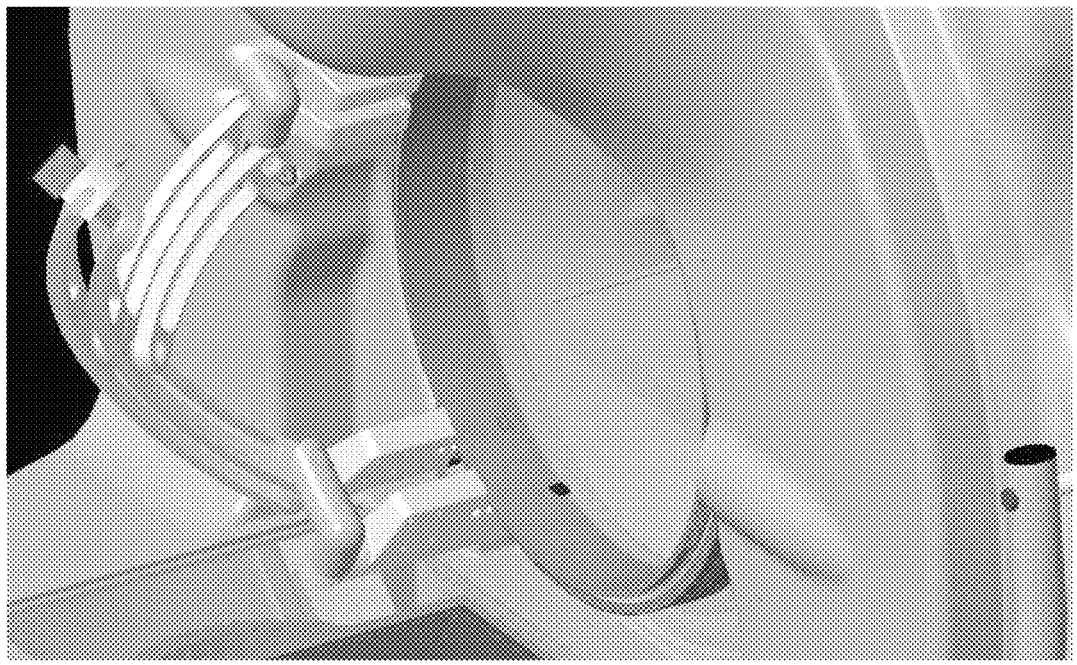
FIGS. 29A-29B show an option to sterilize the distal section of a link.
Figure 29B:
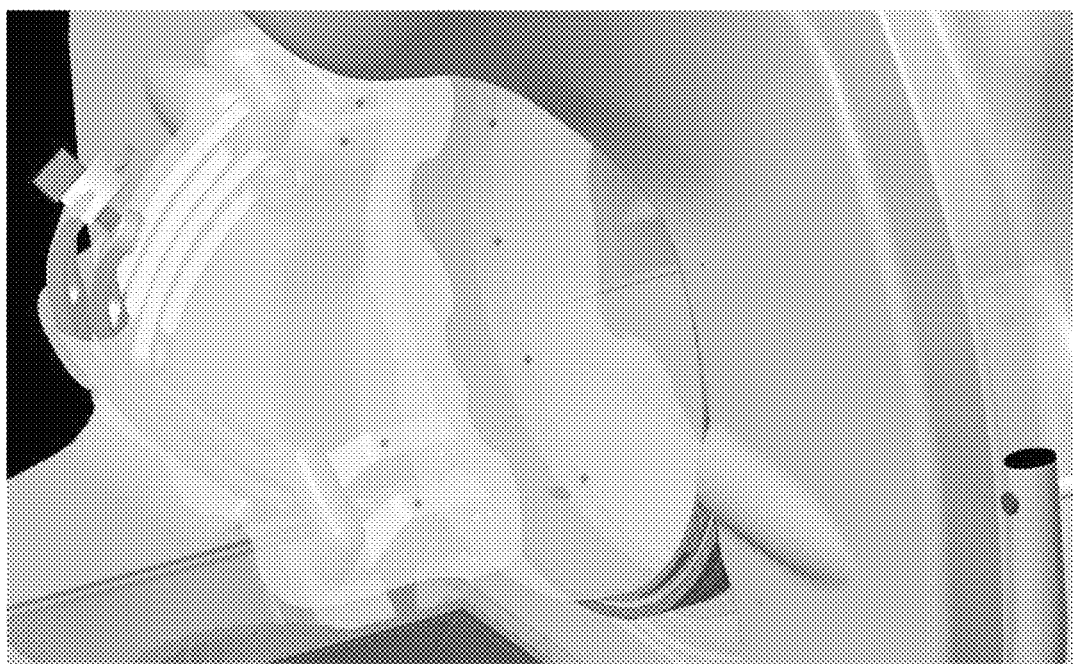

Other modifications are possible. FIGS. 28A-28B show a modification of the links holding the end effector such that the end effector can get closer to the patient's head. FIGS. 29A-29B show an option in which the distal section of the link is removable and able to be sterilized. The robot arm can be covered to allow the sterilization of the distal section. Alternately, the full link set or robotic arm may be removable and able to be sterilized. The movable (motorized) columns can be covered to allow for such sterilization.

Figure 30A:
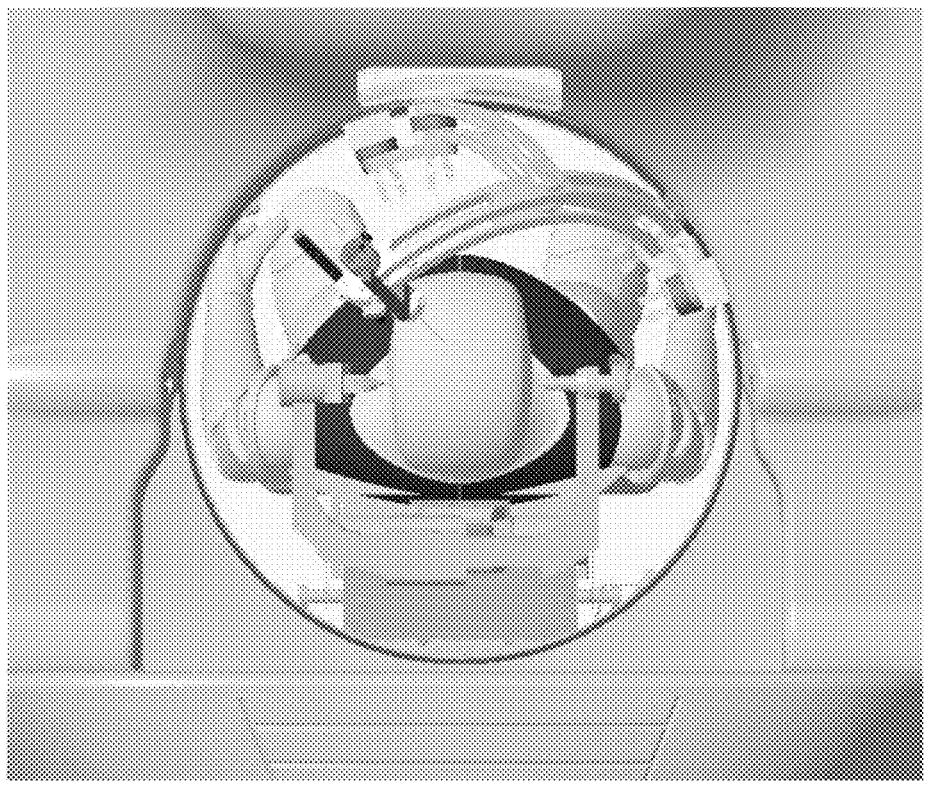
FIGS. 30A-30B show other views of the stereotactic device in a medical imaging bore.
Figure 30B:
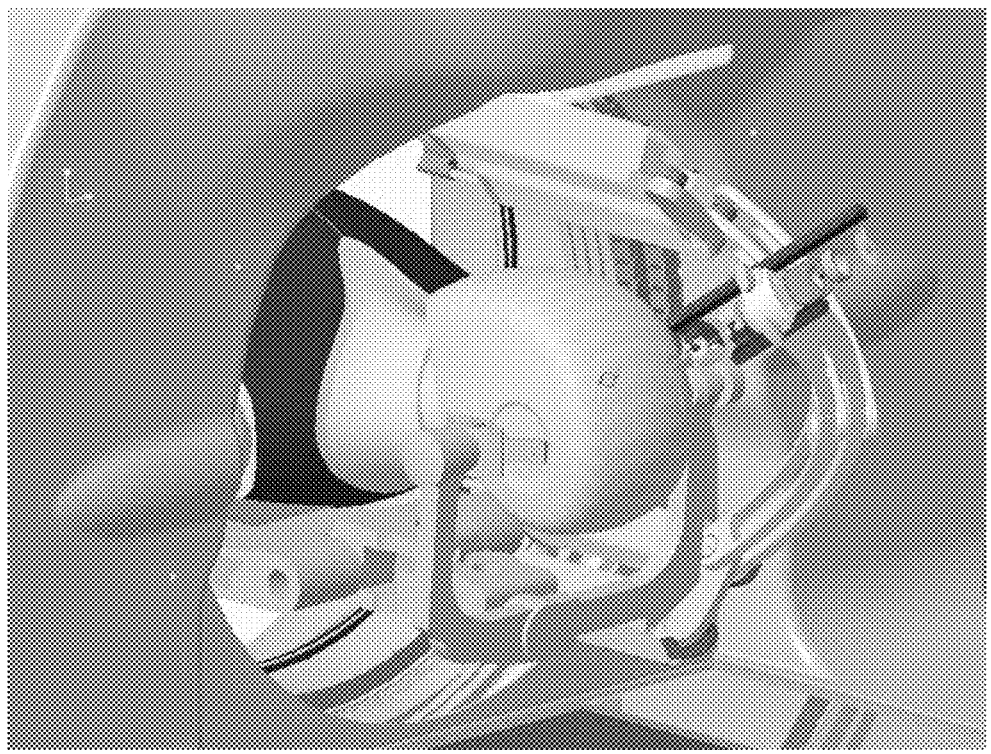
Figure 31A:
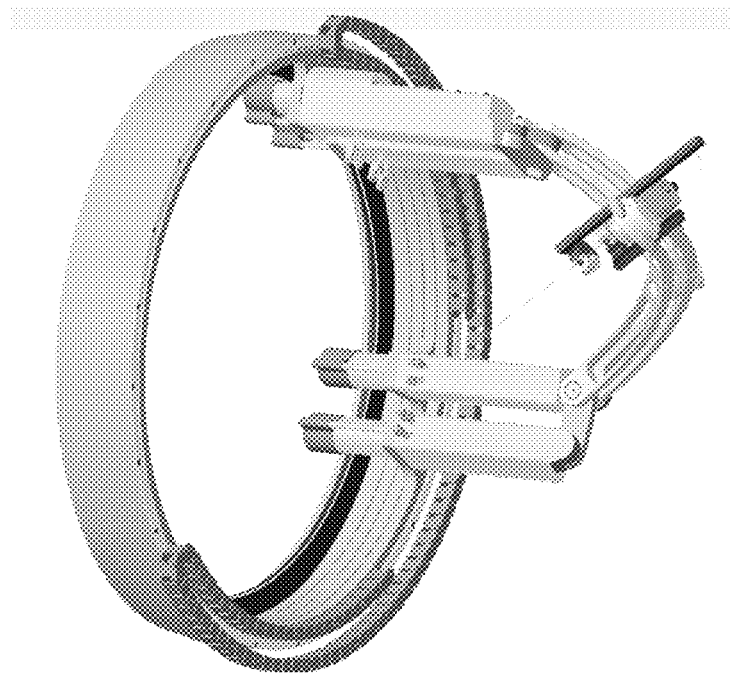
FIGS. 31A-31B show other views of the stereotactic device.
Figure 31B:
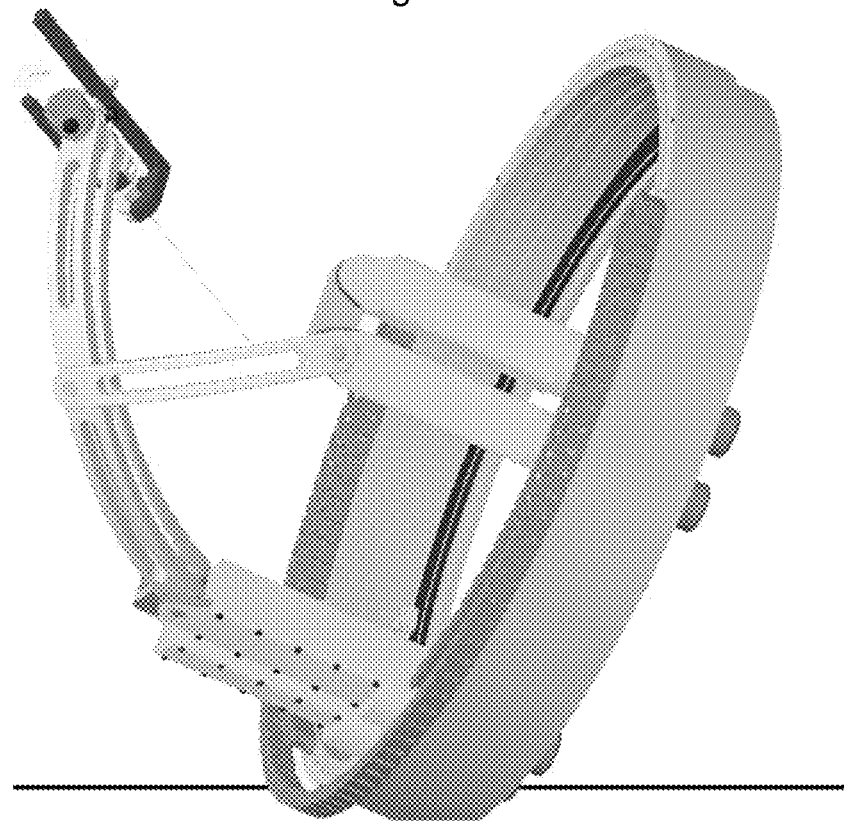
Figure 32:
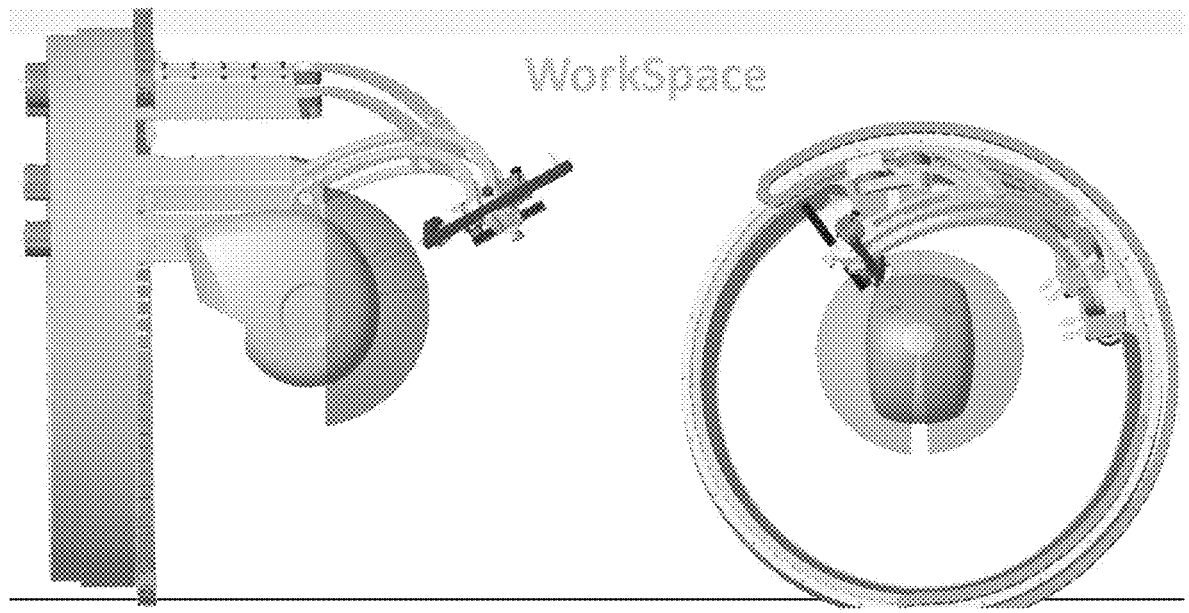
FIG. 32 shows an exemplary workspace or zone of operation in which the stereotactic device operates.
Figure 33A:
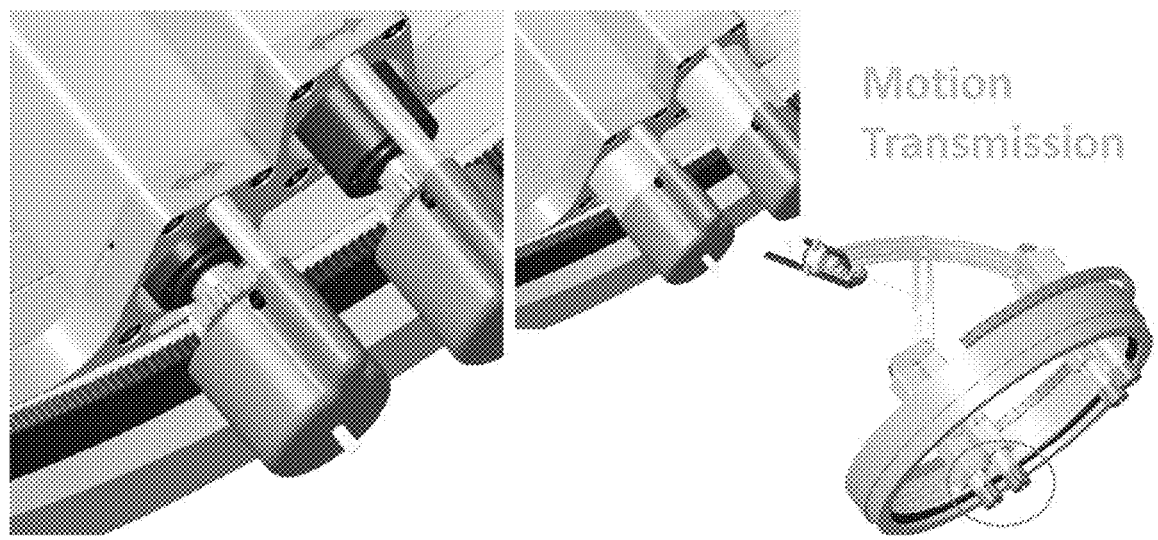
FIGS. 33A-33B show an exemplary drive means for the stereotactic device.
Figure 33B:
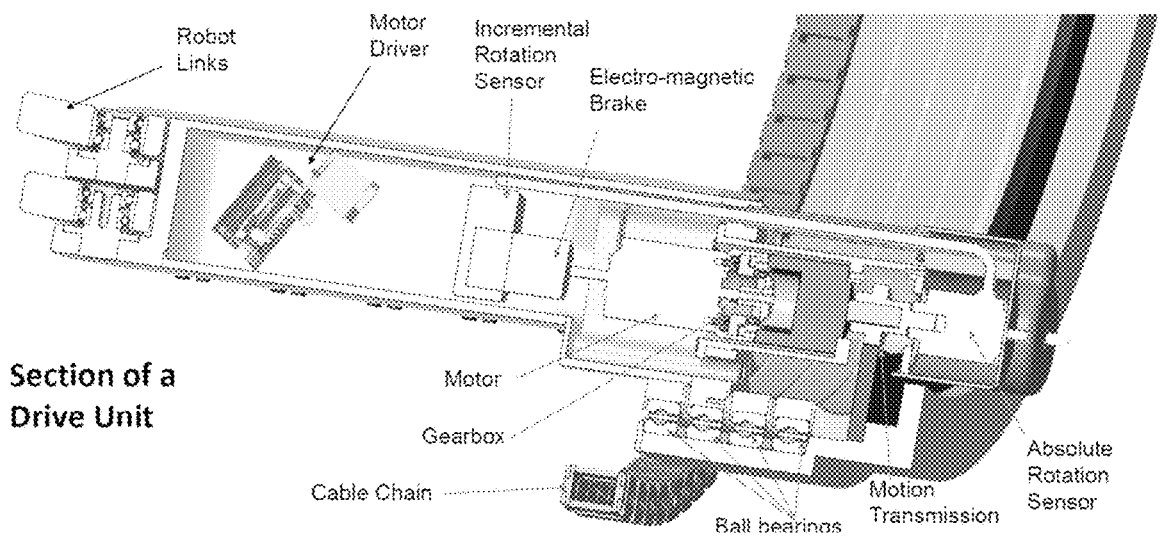
Figure 34:
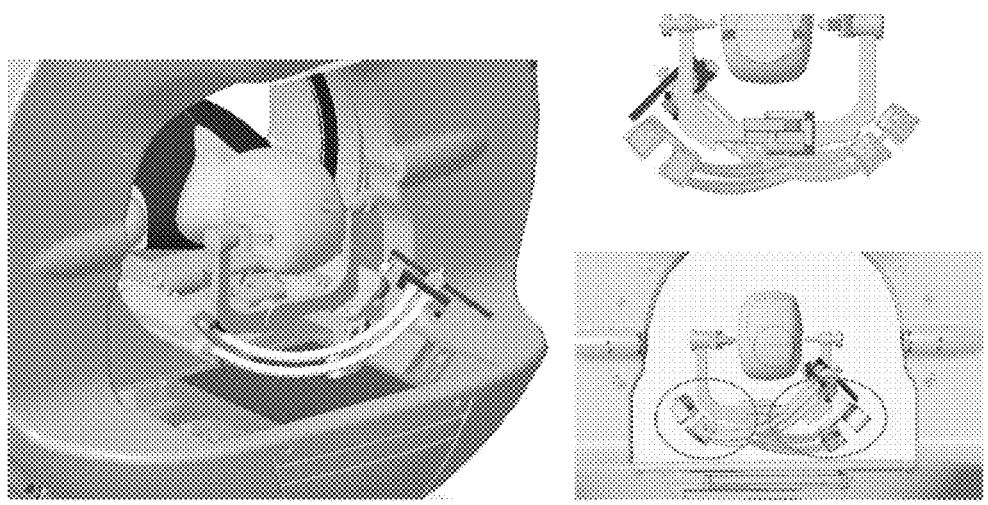
FIG. 34 shows how the stereotactic device may avoid interference with a frame during surgery.

Other views and embodiments are shown in FIGS. 30A-35. FIGS. 30A-30B show other views of the stereotactic device in a medical imaging bore. FIGS. 31A-31B show other views of the stereotactic device. FIG. 32 shows an exemplary workspace or zone of operation in which the stereotactic device operates. FIG. 33A shows an exemplary motion transmission means for the stereotactic device. FIG. 33B shows an exemplary drive unit section for stereotactic device movement. FIG. 34 shows how the stereotactic device may avoid interference with a frame during surgery.

Figure 35:
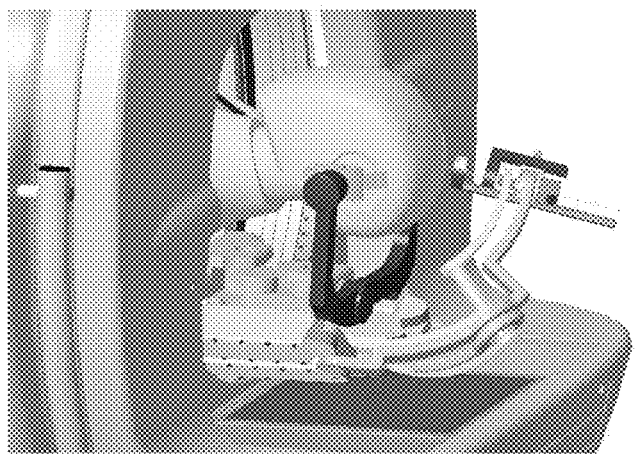
FIG. 35 illustrates exemplary positions for and embodiments of the stereotactic device.
Figure 35:
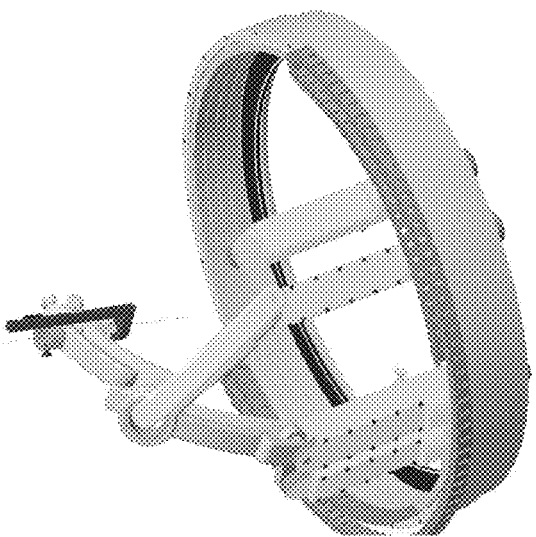
Figure 35:
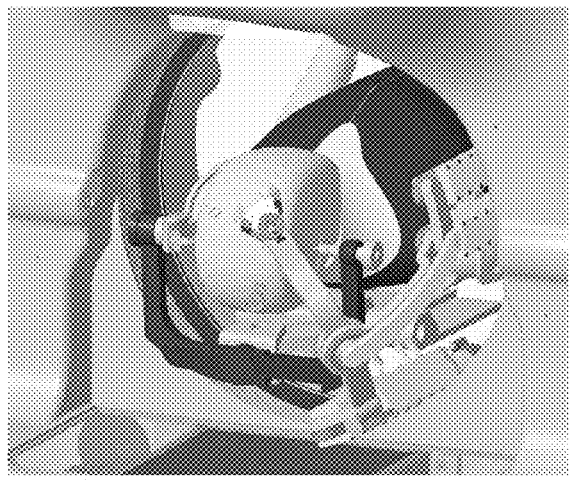
Figure 35:
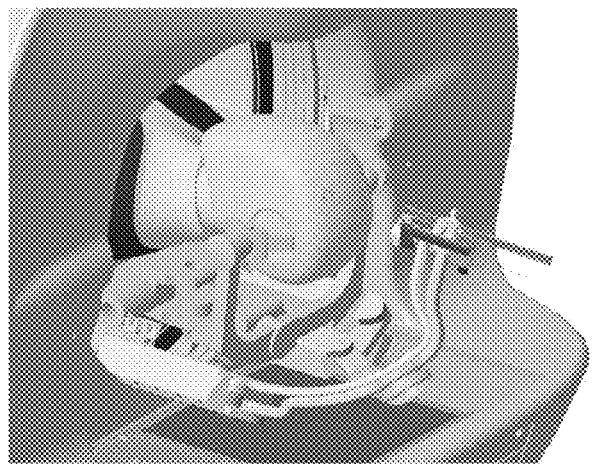

FIG. 35 illustrates exemplary positions for and embodiments of the stereotactic device.

The stereotactic device can be used in other, non-neurosurgical applications, such as thoracic, abdominal, pelvic and extremities (for purposes of diagnostic sampling and/or biopsies), and therapeutics (energy delivery, destructive, other).

Figure 36A:
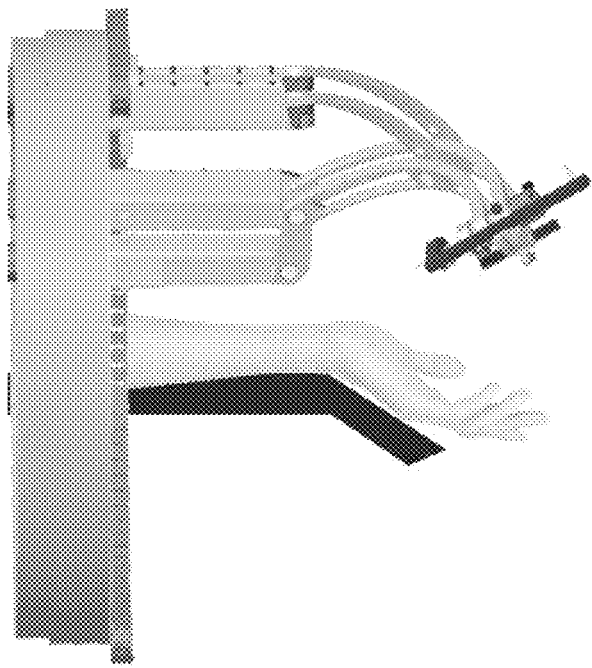
FIGS. 36A-36C show the stereotactic device used to operate on extremities.
Figure 36B:
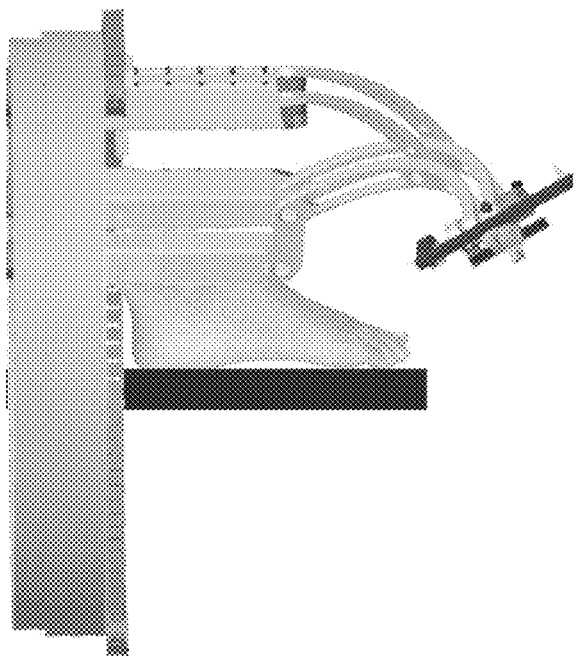
Figure 36C:
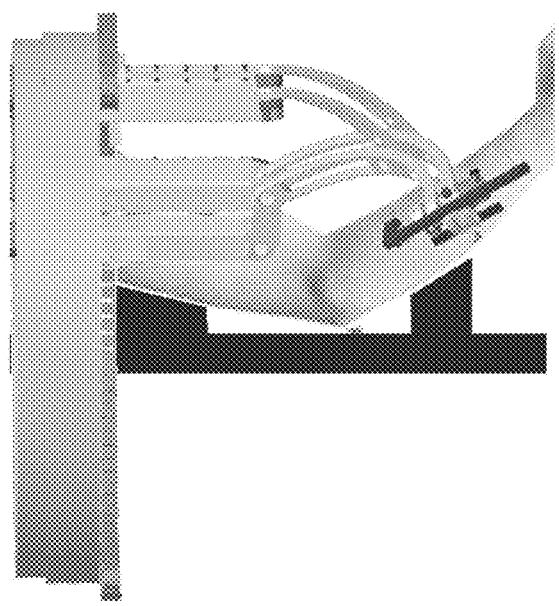

FIGS. 36A-36C show the stereotactic device used to operate on extremities, such as the hand, foot, arm, and elbow. Surgery on a foot may include, for example, miniinvasive surgery (MIS) for bunion and hammertoe reduction. Surgery on a hand may include, for example, carpal tunnel MIS.

Figure 37:
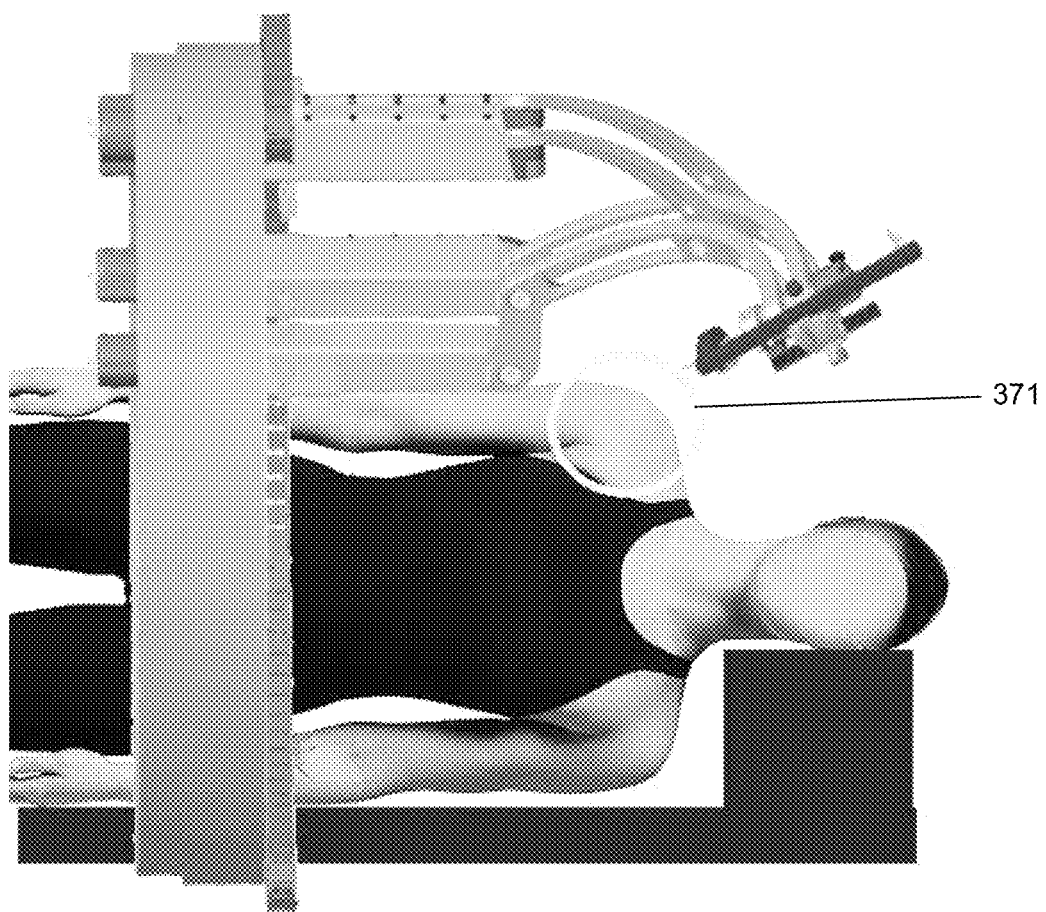
FIG. 37 shows the stereotactic device used to operate on a shoulder.

FIG. 37 shows the stereotactic device used to operate on a shoulder. This figure reiterates that the part to be treated should be in the center of the sphere identified by the stereotactic device. Thus, for a shoulder, for example, the bore in the imaging device should be able to accommodate the body part and the stereotactic device, so the size of the bore may be at least the double the distance shoulder to shoulder. FIG. 37 shows interventional area 371 and the position of the body with respect to the device.

Aspects of the present invention may be embodied in the form of a method, apparatus, or a system. Systems for performing brain surgery have been described that provide free access to a patient's head with high precision, repeatability, and reduced encumbrance. A system can include an apparatus (e.g., a stereotactic device) that includes a first link and a second link, where the first link can be linked to the second link by a hinge, providing two degrees of freedom. One or more end effectors can be positioned at the end of a link and move along a spherical surface. In certain embodiments, each link can be coupled to a slider to provide independent motions of the links. In certain other embodiments, the links can be coupled to two coaxial and coplanar rings. Two vertical columns can be mounted on the two rings. In certain other embodiments, four degrees of freedom can be provided by coupling two stereotactic devices resulting in four concentric rings. End effectors positioned on the links can be moved along two concentric spheres.

The methods and apparatuses described above can be used in conjunction with virtual reality headsets and software for surgical visualization, planning, validation, and verification. For example, virtual reality can be used before or during a surgery to plan steps and identify potential issues or obstacles that are forthcoming.

The above discussion is meant to illustrate the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. An apparatus for performing robot-assisted surgery, comprising:
a first link including a first end and a second end;
a second link including a first end and a second end, wherein the first end of the second link is coupled to the first link by a hinge; and
an end effector positioned at the first end of the first link, wherein the end effector is configured to trace along a surface,
wherein:
the second end of the first link is coupled to a first ring;
the second end of the second link is coupled to a second ring,
the first ring is located external to the second ring; and
the first ring and the second ring are coaxial and coplanar.

2. The apparatus of claim 1, wherein the surface is spherical or hemispherical.

3. The apparatus of claim 1, wherein the first link is coupled to a first slider.

4. The apparatus of claim 1, wherein the second link is coupled to a second slider.

5. The apparatus of claim 1, wherein the first ring is connected to a first actuator and the second ring is connected to a second actuator, and wherein the first actuator and the second actuator are controlled independently.

6. The apparatus of claim 1, further comprising:
a first column including a first end and a second end; and
a second column including a first end and a second end,
wherein:
the first end of the first column is coupled to the second end of the first link;
the first end of the second column is coupled to the second end of the second link;
the second end of the first column is coupled to a first ring; and
the second end of the second column is coupled to a second ring.

7. The apparatus of claim 6, wherein the first column is connected to a first actuator and the second column is connected to a second actuator, the first actuator and the second actuator being controlled independently.

8. The apparatus of claim 1, wherein the first ring and the second ring are perpendicular to the ground.

9. The apparatus of claim 8, wherein the apparatus is integrated in a CT bore.

10. The apparatus of claim 1, wherein the end effector includes a removable section.

11. The apparatus of claim 10, wherein the removable section is disposable.

12. The apparatus of claim 1, wherein the end effector includes a surgical instrument holder.

13. The apparatus of claim 12, further comprising a first spherical joint on the end effector that is configured to adjust orientation of the surgical instrument holder.

14. The apparatus of claim 13, further comprising a passive arm that includes a fixed passive arm support and a foldable end, wherein the foldable end includes a foldable end spherical joint aligned with the first spherical joint to orient a surgical instrument.

15. A system comprising the apparatus of claim 1 and an imaging device.

16. The system of claim 15, wherein the imaging device is a CT scanner.

17. A system for performing surgery, comprising:
an internal apparatus comprising:
a first link including a first end and a second end;
a second link including a first end and a second end, wherein the first end of the second link is coupled to the first link by a first hinge; and
a first end effector positioned at the first end of the first link, wherein the first end effector is configured to trace along a surface,
wherein the second end of the first link is coupled to a first ring, the second end of the second link is coupled to a second ring, and the first ring is located external to the second ring; and
an external apparatus comprising:
a third link including a first end and a second end;
a fourth link including a first end and a second end, wherein the first end of the fourth link is coupled to the third link by a second hinge;
a second end effector positioned at the first end of the third link, wherein the second end effector is configured to trace along the surface; and
the second end of the third link is coupled to a third ring and the second end of the fourth link is coupled to a fourth ring, wherein the third ring is located external to the fourth ring,
and wherein the first ring, the second ring, third ring, and the fourth ring are coaxial and coplanar.

18. The system of claim 17, wherein the surface is spherical or hemispherical.

19. The system of claim 17, wherein the first end effector and the second end effector are configured to trace along two concentric spheres.

20. The system of claim 17, where the first ring is connected to a first actuator, the second ring is connected to a second actuator, the third ring is connected to a third actuator, and the fourth ring is connected to a fourth actuator, and wherein the first actuator, the second actuator, the third actuator, the fourth actuator are controlled independently.

21. The system of claim 17, wherein the internal apparatus is integrated in a CT bore.

22. The system of claim 17, wherein the first end effector includes a surgical instrument holder.

23. The system of claim 22, wherein the internal apparatus further comprises a first spherical joint on the first end effector and the first spherical joint adjusts orientation of the surgical instrument holder.

24. The system of claim 22, further comprising a first fixed passive arm that includes a first fixed passive arm support and a first foldable end, wherein the first foldable end includes a first foldable end spherical joint aligned with the first spherical joint to orient a surgical instrument.

25. The system of claim 17, further comprising an imaging device.

26. The system of claim 25, wherein the imaging device is a CT scanner.

* * * * *